(12) United States Patent
Aguiar et al.

(10) Patent No.: US 11,564,831 B1
(45) Date of Patent: Jan. 31, 2023

(54) SYSTEM AND METHODS FOR MONITORING AND/OR CONTROLLING TEMPERATURE IN A THERAPY DEVICE

(71) Applicant: Hyper Ice, Inc., Irvine, CA (US)

(72) Inventors: Alexander Joseph Aguiar, Irvine, CA (US); Daniel Royal Evans, Irvine, CA (US); Robert Glen Edwards, Irvine, CA (US); Trevor Austin Kerth, Irvine, CA (US)

(73) Assignee: Hyper Ice, Inc., Irvine, CA (US)

( * ) Notice: Subject to any disclaimer, the term of this patent is extended or adjusted under 35 U.S.C. 154(b) by 0 days.

(21) Appl. No.: 17/307,981

(22) Filed: May 4, 2021

Related U.S. Application Data

(60) Provisional application No. 63/090,987, filed on Oct. 13, 2020.

(51) Int. Cl.
*A61F 7/02* (2006.01)
*A61F 7/00* (2006.01)

(52) U.S. Cl.
CPC .............. *A61F 7/02* (2013.01); *A61F 7/007* (2013.01); *A61F 2007/0075* (2013.01);
(Continued)

(58) Field of Classification Search
CPC .............. A61F 7/007; A61F 2007/0075; A61F 2007/0093; A61F 2007/0094;
(Continued)

(56) References Cited

U.S. PATENT DOCUMENTS 4,962,761 A 10/1990 Golden
5,080,089 A 1/1992 Mason et al.
(Continued)

FOREIGN PATENT DOCUMENTS

CA 2356993 A1 7/2000

OTHER PUBLICATIONS

U.S. Appl. No. 15/818,308 U.S. Pat. No. 10,406,024, Wearable Temperature Therapy System and Method, filed Nov. 20, 2017.
(Continued)

*Primary Examiner* — Kaitlyn E Smith
*Assistant Examiner* — Bradford C. Blaise
(74) *Attorney, Agent, or Firm* — Goodwin Procter LLP

(57) ABSTRACT

A temperature therapy system and a method for temperature control for such a temperature therapy system are disclosed. According to one embodiment, a temperature therapy system has a retention mechanism and a plurality of temperature modulation systems attached to the retention mechanism, wherein each of the plurality of temperature modulation systems comprises a thermoelectric cooler. The wearable personal temperature therapy system may have a plurality of temperature sensors and a plurality of conductive flags, wherein each of the plurality of conductive flags is adhered to a respective thermoelectric cooler and a respective temperature sensor. The wearable personal temperature therapy system may have a control module electrically coupled to each of the plurality of temperature modulation systems and each of the plurality of temperature sensors, wherein each of the temperature modulation systems is controlled based on a control voltage applied to the thermoelectric cooler of the respective temperature modulation system.

9 Claims, 12 Drawing Sheets

(52) U.S. Cl.
CPC ............. *A61F 2007/0094* (2013.01); *A61F 2007/0096* (2013.01); *A61F 2007/0233* (2013.01)

(58) Field of Classification Search
CPC ...... A61F 2007/0095; A61F 2007/0096; A61F 7/02; A61F 2007/0233
See application file for complete search history.

(56) References Cited

U.S. PATENT DOCUMENTS

| | | | |
|---|---|---|---|
| 5,800,490 A * | 9/1998 | Patz | ............ A61F 7/007 607/108 |
| 5,847,929 A | 12/1998 | Bernier et al. | |
| 5,865,841 A | 2/1999 | Kolen et al. | |
| 5,871,526 A | 2/1999 | Gibbs et al. | |
| 6,818,012 B2 | 11/2004 | Ellingboe | |
| 8,425,579 B1 | 4/2013 | Edelman et al. | |
| 10,406,024 B2 | 9/2019 | Evans et al. | |
| 2003/0097845 A1 * | 5/2003 | Saunders | ............ A61F 7/007 62/3.3 |
| 2005/0075593 A1 | 4/2005 | Smith et al. | |
| 2005/0193742 A1 * | 9/2005 | Arnold | ............ A62B 17/005 62/3.5 |
| 2008/0046047 A1 | 2/2008 | Jacobs | |
| 2008/0188915 A1 * | 8/2008 | Mills | ............ A61F 7/007 607/112 |
| 2010/0198322 A1 | 8/2010 | Joseph et al. | |
| 2012/0179231 A1 | 7/2012 | Dewaegenaere | |
| 2013/0085552 A1 * | 4/2013 | Mandel | ............ A61F 7/007 607/99 |
| 2013/0087180 A1 | 4/2013 | Stark et al. | |
| 2014/0102204 A1 | 4/2014 | Akiyama et al. | |
| 2014/0260330 A1 | 9/2014 | Karlstedt | |
| 2014/0352325 A1 * | 12/2014 | Brown | ............ F25B 21/02 62/3.2 |
| 2015/0101788 A1 | 4/2015 | Smith et al. | |
| 2017/0325975 A1 | 11/2017 | LeRoy et al. | |
| 2018/0098903 A1 | 4/2018 | Vergara et al. | |
| 2018/0110266 A1 | 4/2018 | Lee et al. | |
| 2018/0147086 A1 * | 5/2018 | Evans | ............ A61F 7/02 |

OTHER PUBLICATIONS

U.S. Appl. No. 16/525,407, Wearable Temperature Therapy System and Method, filed Jul. 29, 2019.

U.S. Appl. No. 17/308,012, Temperature Modulation Assembly and a Multi-layer Retention Mechanism for a Temperature Therapy Device, filed May 4, 2021.

Jordan, D. et al., "Electric Hot/Cold Wrap", Mechanical Engineering Capstone Projects, Northeastern Univ., (Dec. 2010), retrieved from the internet, URL:http://www.mie.neu.edu/mie/capstone/mechanical-engineering-capstone-projects, 12 pages.

* cited by examiner

US 11,564,831 B1

SYSTEM AND METHODS FOR MONITORING AND/OR CONTROLLING TEMPERATURE IN A THERAPY DEVICE

CROSS-REFERENCE TO RELATED APPLICATIONS

This application claims priority and benefit from U.S. Provisional Application No. 63/090,987, titled "Flexible Heat Spreader System and Method" and filed on Oct. 13, 2020, which is hereby incorporated by reference herein in its entirety.

TECHNICAL FIELD

The present disclosure relates generally to the physical therapy and/or temperature therapy field, and more specifically to systems and methods for monitoring and/or controlling the temperature of a therapy device.

BACKGROUND

Temperature therapy or "thermal therapy" (e.g., the application of heat and/or cold to the body) has been shown to be effective in injury recovery, helping to expedite the healing process while reducing pain, inflammation, and joint stiffness. Localized cooling can induce vasoconstriction with reflexive vasodilation and/or reduce bleeding, inflammation, metabolism, muscle spasm, pain, enzymatic activity, oxygen demand, and/or swelling in areas of the body affected by soft tissue trauma or injury. Localized heating can increase blood flow, decrease sensation of pain, increase local tissue metabolic rate, increase the rate of healing, and/or facilitate the stretching of tissue.

Conventional temperature therapy devices generally have limited functionality for accurately monitoring device operating temperature(s) and resulting temperature(s) at a body region of a user. In general, failure to properly monitor and control the temperature of a therapy device can impede the delivery of the above-described therapeutic effects of temperature therapy and ultimately interfere with injury recovery. In extreme cases, failure to properly monitor and control the temperature of a therapy device can cause new injuries such as burns or frostbite.

The foregoing examples of the related art and limitations therewith are intended to be illustrative and not exclusive, and are not admitted to be "prior art." Other limitations of the related art will become apparent to those of skill in the art upon a reading of the specification and a study of the drawings.

SUMMARY

A system for monitoring and/or controlling temperature for a temperature therapy device is disclosed. According to one embodiment, a wearable personal temperature therapy system for placement at a body region of a user may have a retention mechanism and a plurality of temperature modulation systems attached to the retention mechanism, wherein each of the plurality of temperature modulation systems comprises a thermoelectric cooler having a first side and a second side opposing the first side. The wearable personal temperature therapy system may have a plurality of temperature sensors and a plurality of conductive flags, wherein each of the plurality of conductive flags comprises a thermally conductive material, has a first side and a second side opposing the first side, and has a first end and a second end, wherein the first side comprises an adhesive material, and wherein for each of the plurality of conductive flags, the first side of the first end is adhered to the first side of a respective thermoelectric cooler of the plurality of thermoelectric coolers, and wherein the first side of the second end is adhered to a respective temperature sensor of the plurality of temperature sensors. The wearable personal temperature therapy system may have a control module electrically coupled to each of the plurality of temperature modulation systems and each of the plurality of temperature sensors, wherein each of the temperature modulation systems is operable between a cooling mode and a heating mode based on a control voltage applied to the thermoelectric cooler of the respective temperature modulation system.

The above and other preferred features, including various novel details of implementation and combination of events, will now be more particularly described with reference to the accompanying figures and pointed out in the claims. It will be understood that the particular systems and methods described herein are shown by way of illustration only and not as limitations. As will be understood by those skilled in the art, the principles and features described herein may be employed in various and numerous embodiments without departing from the scope of any of the present inventions. As can be appreciated from foregoing and following description, each and every feature described herein, and each and every combination of two or more such features, is included within the scope of the present disclosure provided that the features included in such a combination are not mutually inconsistent. In addition, any feature or combination of features may be specifically excluded from any embodiment of any of the present inventions.

BRIEF DESCRIPTION OF THE DRAWINGS

The accompanying figures, which are included as part of the present specification, illustrate the presently preferred embodiments and together with the general description given above and the detailed description of the preferred embodiments given below serve to explain and teach the principles described herein.

Figure 1A:
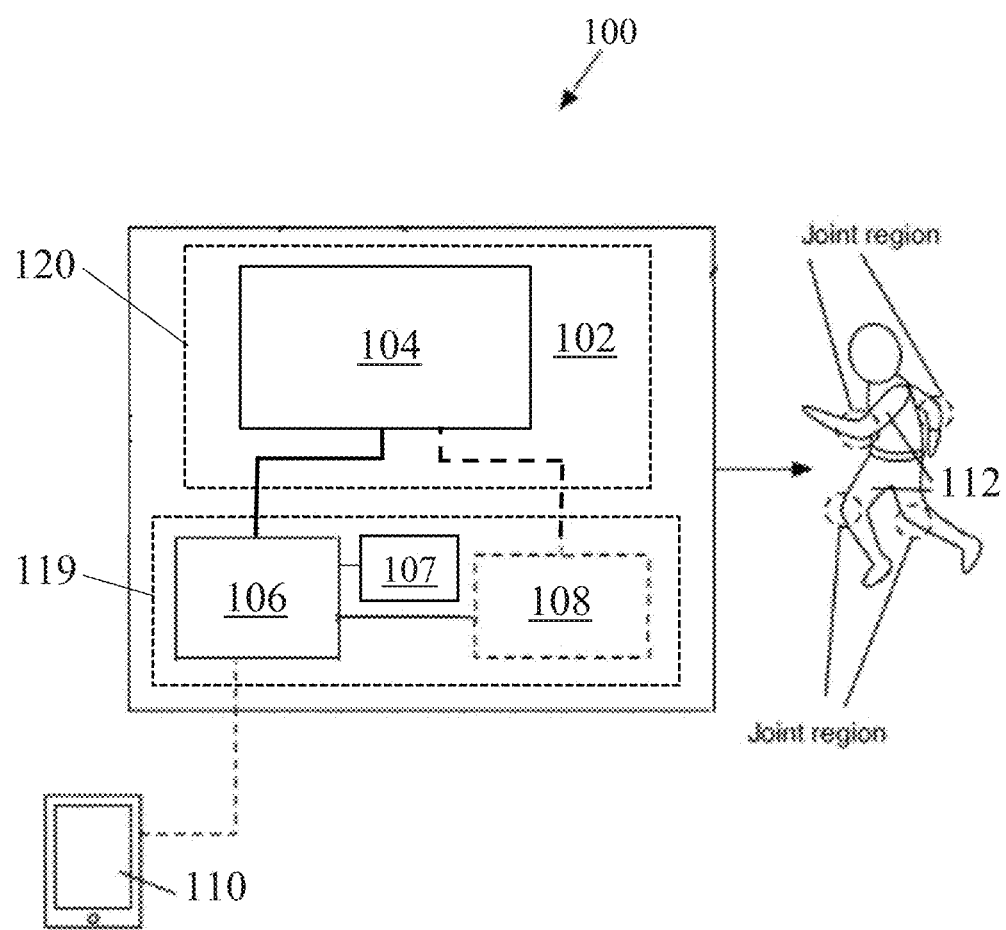
FIG. 1A illustrates a block diagram of a temperature therapy device, according to some embodiments.

While the present disclosure is subject to various modifications and alternative forms, specific embodiments thereof have been shown by way of example in the drawings and will herein be described in detail. The present disclosure should be understood to not be limited to the particular forms disclosed, but on the contrary, the intention is to cover all modifications, equivalents, and alternatives falling within the spirit and scope of the present disclosure.

DETAILED DESCRIPTION

A system for determining and controlling temperature for a temperature therapy device is disclosed.

Motivations for and/or Benefits of Some Embodiments

Conventional temperature therapy devices generally have limited functionality for accurately monitoring device operating temperature(s) and resulting temperature(s) at a body region of a user. This deficiency is often due to a measurement disconnect between device operating temperature(s) and temperature(s) at a body region. Such a measurement disconnect can occur from inefficient component placement within a therapy device, such that temperature sensing components are unable to accurately track temperature(s) at a body region. Thus far, attempts to place temperature sensing components closer to the body have resulted in user discomfort or drift from desired operating temperature(s). Further, a measurement disconnect can result from faulty control methods for mapping device operating temperature(s) to temperature(s) at a body region, where control methods fail to account for thermal buffering effects from a body region during therapeutic operation of the therapy device. An inability to accurately monitor temperature(s) at a body region can lead to ineffective therapeutic techniques, as well as possible injury to a user from exposure to extreme operating temperatures. Therefore, typical temperature therapy devices may disrupt the required rest/recovery of a user, and can contribute to hindering or even extending recovery times. Thus, there is a need for improved temperature therapy devices featuring improved placement of temperature measurement components to better track operating temperature(s), as well as improved methods for monitoring and/or controlling the temperature(s) applied to a body region of a user.

Overview of a Temperature Therapy Device

Referring to FIG. 1A, a block diagram for a temperature therapy device 100 is presented, according to some embodiments. In some embodiments, the temperature therapy device 100 can include a multi-layer retention mechanism 102, a temperature modulation system 104 retained by the multi-layer retention mechanism 102, and a control module 106 communicatively coupled to the temperature modulation system 104 and retained by the multi-layer retention mechanism 102. In some embodiments, the multi-layer retention mechanism 102 can include a flexible substrate. The multi-layer retention mechanism may include one or more of straps, buckles, and fabric layers. In an example, the multi-layer retention mechanism 102 can include a plate, a heat spreader and a flexible fabric. In an embodiment, the temperature modulation system 104 can include a fan, a heatsink and a thermoelectric cooler (TEC). In some embodiments, the temperature therapy device 100 can include a component mounting system 120. In some embodiments, the component mounting system 120 can include the multi-layer retention mechanism 102 and the temperature modulation system 104. In some embodiments, a temperature therapy device 100 can include one or more component mounting systems 120. The temperature therapy device 100 can also include a power supply module 108 retained by the multi-layer retention mechanism 102 and electrically coupled to the temperature modulation system 104 and the control module 106, a client application executing at a mobile device 110 in communication with the control module 106, and any other suitable components. In some embodiments, the control module 106 and the power supply module 108 can be combined into a combined control and power supply module 119. In some embodiments, the temperature therapy device 100 can include and/or can also be referred to as a wearable cooling and heating system.

Figure 1B:
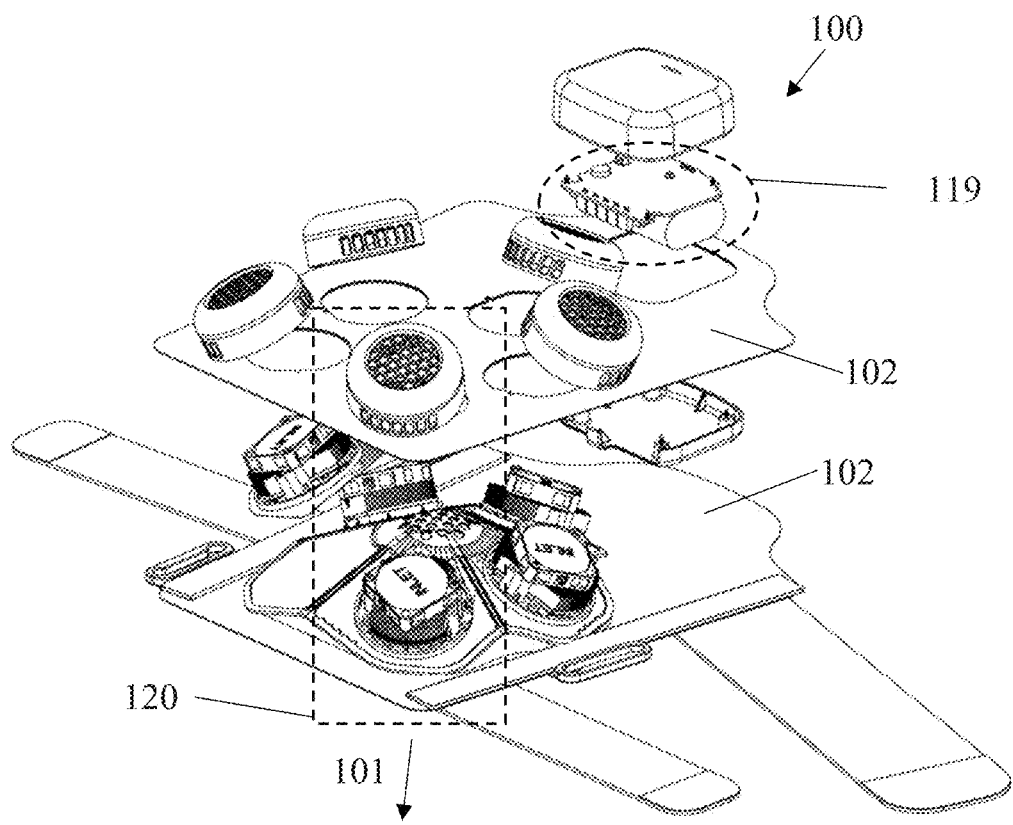
FIG. 1B illustrates an exploded view of an exemplary temperature therapy device, according to some embodiments.

Referring to FIG. 1B, an exploded view of an exemplary temperature therapy device is presented. As shown, the temperature therapy device 100 can include the component mounting system 120, the combined control and power module 119 and a multi-layer retention mechanism 102 described in FIG. 1A. In some embodiments, a temperature sensor 107 can be coupled to the control module 106. The temperature sensor 107 can measure the temperature at the temperature modulation system 104. In some embodiments, the temperature therapy device 100 can include one or more temperature sensors 107.

Functions of a Temperature Therapy Device

Referring again to FIG. 1A, the temperature therapy device 100 can function to provide temperature regulated cold and/or hot therapy to a body region of a user 112, and in specific examples can provide both cold and hot therapy to a body region of the user, using the same device, with rapid transitions between heat and cold therapy provision modes (e.g., heating mode, cooling mode, etc.) of operation. In an example, the temperature therapy device can use the multi-layer retention mechanism 102 and the temperature modulation system 104, each housed within the component mounting system 120, to provide the temperature therapy to a body region of a user 112. The temperature therapy device 100 can also function to regulate the temperature of the hot or cold therapy based on received control instructions (e.g., from a mobile application-based controller, a mobile computing platform, a client application execution thereon, etc.). The temperature therapy device 100 can also function to monitor and/or track parameters of therapy provision, such as the temperature of the hot or cold therapy being provided, the power and/or energy usage of the system during therapy provision, and any other suitable parameters. The temperature therapy device 100 can also function to track user data such as frequency of use (e.g., daily, hourly, monthly, etc.), duration of use (e.g., total duration in minutes, duration on a per-operating-mode basis, duration on a per-contiguoususe basis, etc.) and therapy selection (e.g., heat therapy, cold therapy), and provide tracked user data to an entity (e.g., the user, a physical therapist associated with the user, etc.), in order to guide automated modes of therapy provision to the user.

Referring again to FIGS. 1A and 1B, the temperature therapy device 100 can be positioned at a musculoskeletal region of the user (e.g., a knee region, a lower back region, an elbow region, etc.). However, the temperature therapy device 100 can additionally or alternatively include multiple instances of the temperature therapy device but in the same or different configurations, that can be positioned at disparate regions of the user (e.g., a first knee region, a second knee region, a lower back region, any other suitable musculoskeletal region, any other suitable body region, etc.). The system can preferably be placed around a knee region of a user, arranging one or more temperature modulation systems proximal a knee cap region of a user in a pattern defined by the multi-layer retention mechanism 102. Additionally or alternatively, the temperature therapy device 100 can be placed around a torso region of a user, positioning the temperature modulation system(s) proximal another musculoskeletal region (e.g., a lower back region). The direction 101 at which the temperature therapy device 100 is positioned on a user is shown in FIG. 1B.

Component Mounting System for a Temperature Therapy Device

To effectively position and the temperature therapy components of a temperature therapy device to a user, and provide temperature regulated therapy to a body region of a user 112, it can be beneficial to package together inelastic and elastic components of the temperature therapy device in a compact arrangement.

Figure 1C:
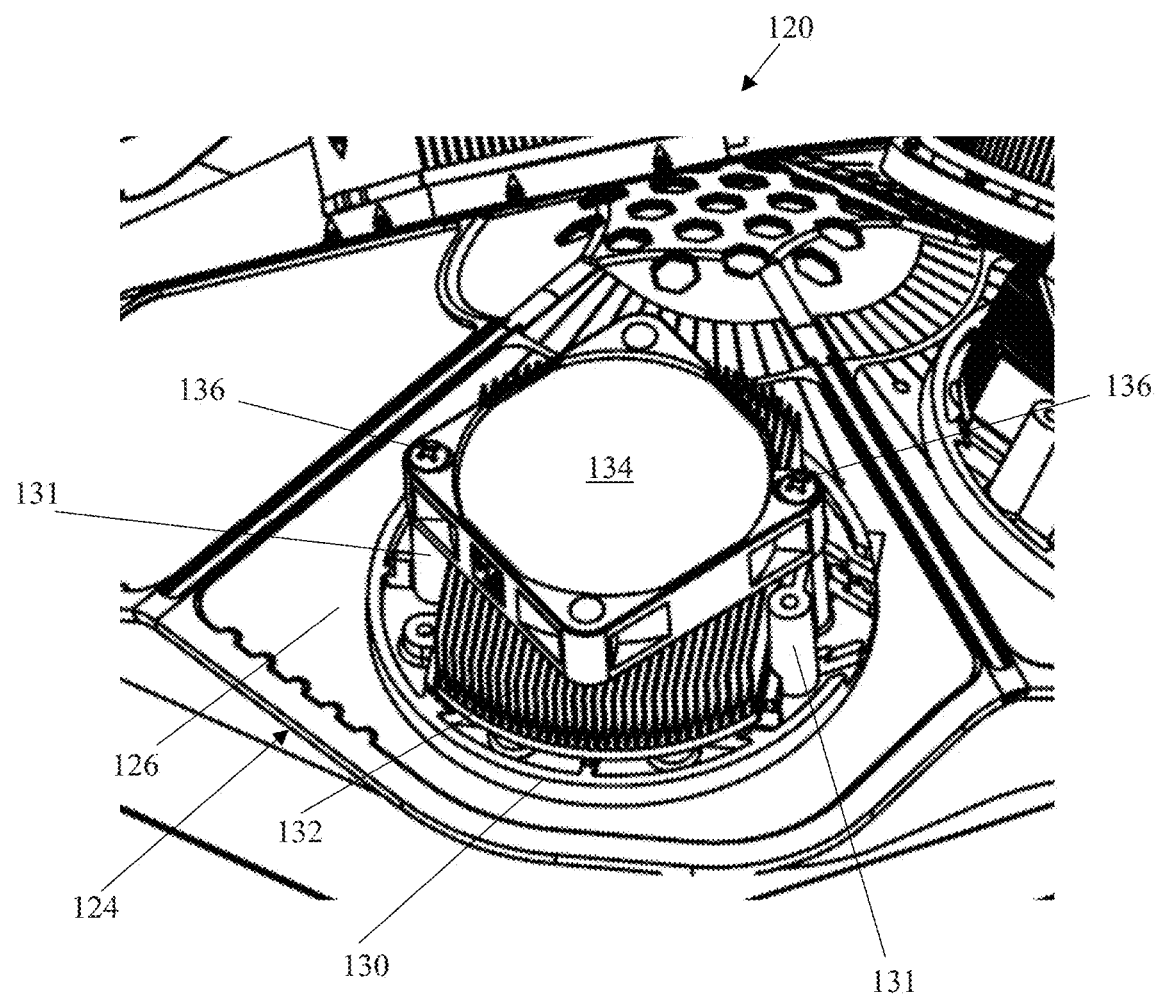
FIG. 1C illustrates a plan view of a partially assembled component mounting system for the temperature therapy device of FIGS. 1A and 1B, according to some embodiments.
Figure 1D:
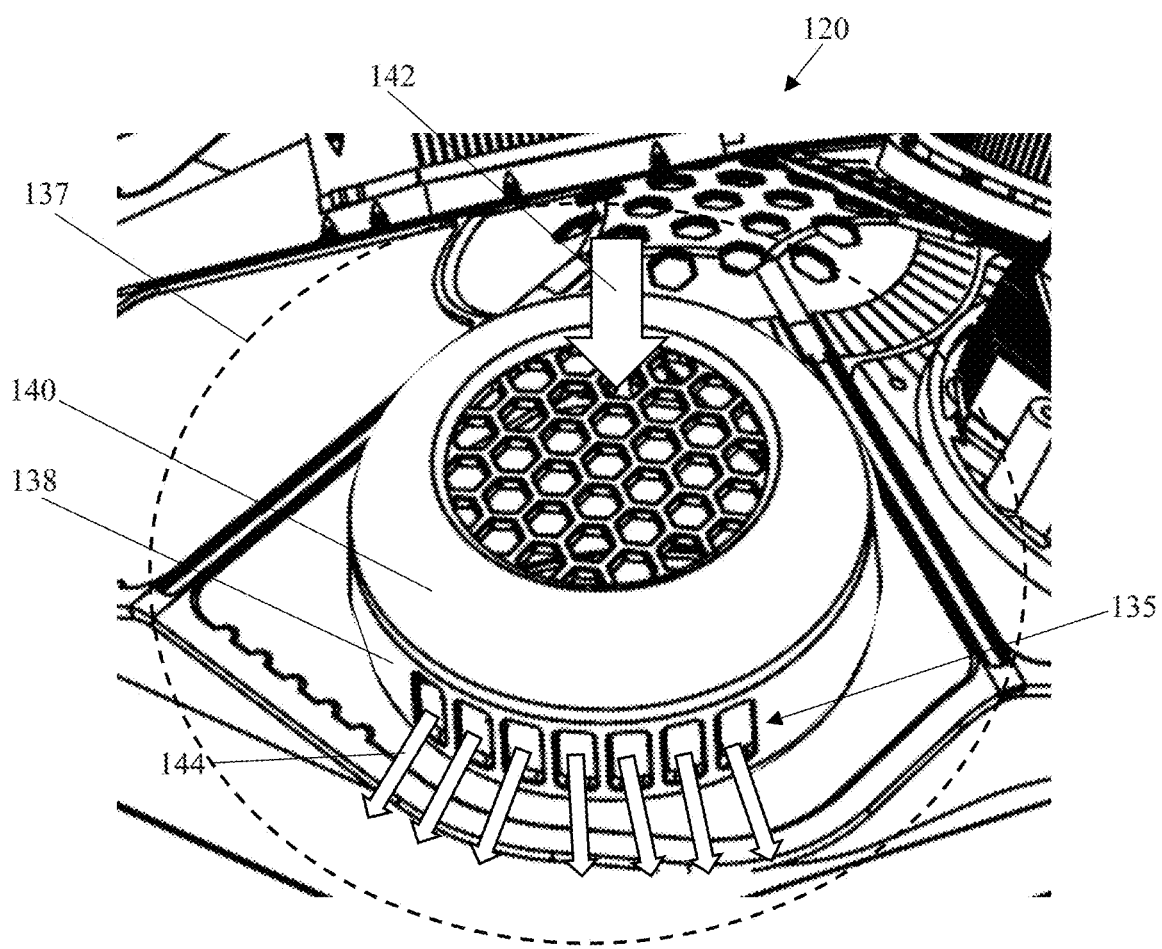
FIG. 1D illustrates a plan view for the component mounting system of FIGS. 1A-1C, according to some embodiments.
Figure 1E:
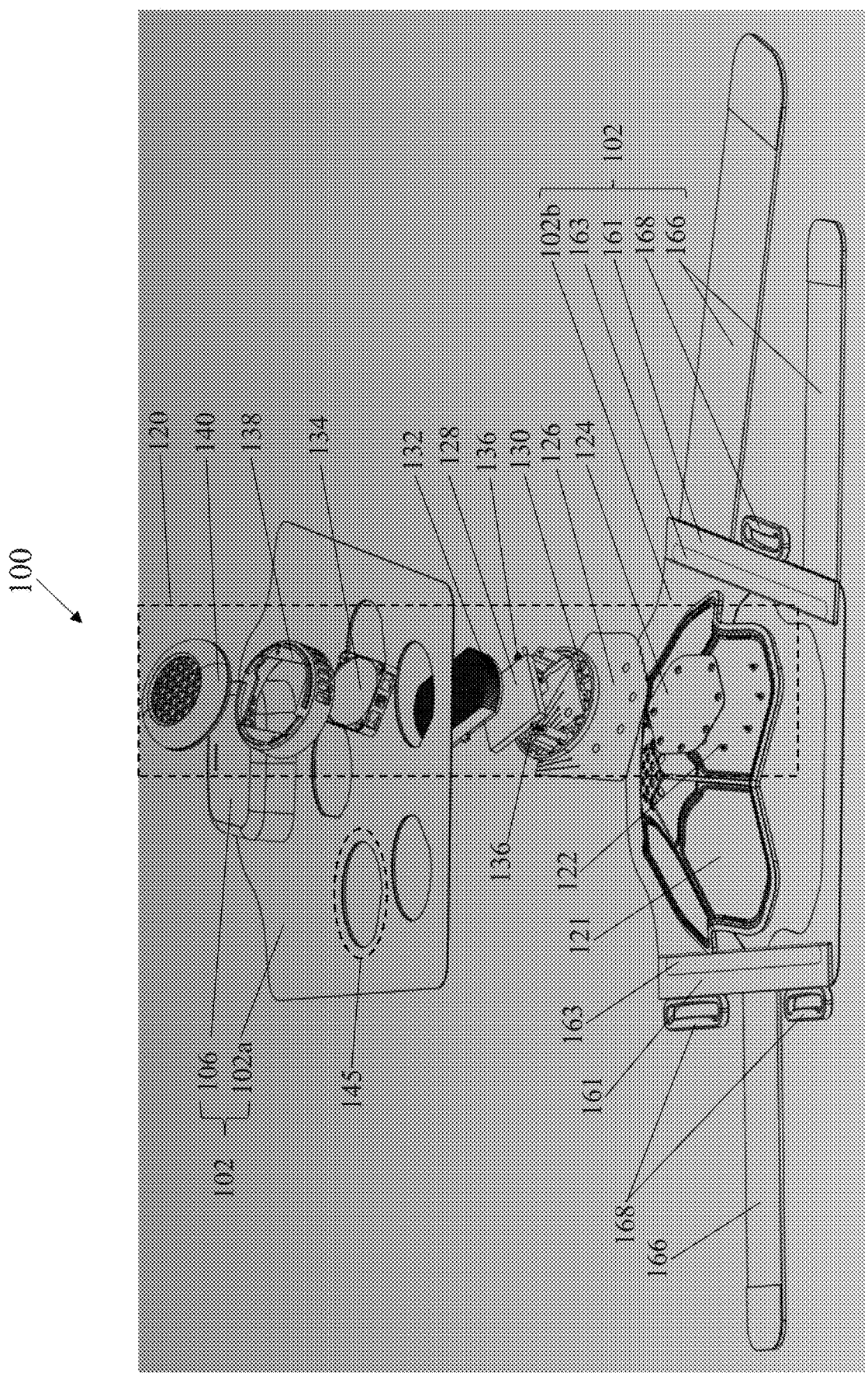
FIG. 1E illustrates an exploded view for the component mounting system of FIGS. 1A-1D, according to some embodiments.

Referring to FIGS. 1C-1E, multiple views of a component mounting system of a temperature therapy device are presented. In FIG. 1C, a plan view of a partially assembled component mounting system 120 is shown to depict the configuration and coupling of the underlying components housed within the component mounting system 120. FIG. 1D is shown to present a view of an assembled component mounting system. FIG. 1E shows an exploded view of the component mounting system.

Referring to FIG. 1C, a plan view of a partially assembled component mounting system for a temperature therapy device 100 is presented. In some embodiments, the component mounting system 120 can include a plate (not shown) and a heat spreader 126 which can be components of the multi-layer retention mechanism 102 of FIG. 1A. The component mounting system 120 can also include a spacer 130, a heatsink 132, and a fan 134 which can be components of the temperature modulation system 104 of FIG. 1A. In some embodiments, the spacer 130 can also be referred to as a mounting component, among other terms. Also shown in FIG. 1C is how the fan 134 is mounted to the spacer 130. In an example, the fan 134 can be held down by screws 136 inserted into columnal structures 131 of the spacer 132. In some embodiments, as shown, the heatsink 132 can be secured between the fan 134 and the spacer 130.

Referring to FIG. 1D, a plan view of an assembled component mounting system 120 is shown. In some embodiments, the component mounting system 120 can include a cap 140 and cover 138. Represented in dotted lines, to show the components underneath, and which will be discussed in more detail below, is a flexible fabric 137. Also shown in FIG. 1D is the direction of the air flow used by the temperature therapy device 100 of FIGS. 1A and 1B to regulate the temperature of the components housed within the component mounting system 120. In some embodiments, for air intake 142 into the component mounting system 120, air is pulled in though cap 140 by the fan 134 into the heatsink, e.g., fan 134 and heatsink 132 of FIG. 1C. In some embodiments, for airflow outtake 144 of the component mounting system 120, the fan 134 pushes air through the heatsink 132, and out of the component mounting system 120 through vents 135 of the cover 138. Furthermore, although the air flow is shown in one direction in the example of FIG. 1D, e.g., intake 142 through the cap 140 and exhaust through the vents 135, the air can flow in the opposite direction. For example, air can flow into the component mounting system through the vents 135 and exit the component mounting system 120 through the cap 140.

Referring to FIG. 1E, an exploded view of the temperature therapy device 100 is presented, according to some embodiments. Referring again to FIG. 1E, the temperature therapy device 100 can include a multi-layer retention mechanism 102, and a component mounting system 120, among other components. As shown, the multi-layer retention mechanism 102 can include a top layer 102a and a bottom layer 102b. The top layer 102a of the multi-layer retention mechanism can include and/or be coupled to a control module 106, similar to that described with reference to FIG. 1B. The bottom layer 124 of the multi-layer retention mechanism can include and/or be coupled to one or more boning mechanisms 163, one or more structural support pieces 161, one or more straps 166, and/or one or more locking mechanisms 168, e.g., similar to those described in FIG. 1B. Furthermore, the top layer 102a can include one or more openings 145, where the edges of the openings 145 can be configured to be received and/or secured by a spacer 130 and cover 138 of the component mounting system 120. In one example, the top layer 102a can include alignment features along edges of the openings 145 that are received by corresponding alignment features of the spacer 130 and the cover 138. The alignment features of the top layer 102a can be used for ensuring the spacer 130, top layer 102a and cover 138 are all correctly aligned and/or mounted together. In some embodiments, the top layer 102a and bottom layer 124 can include a flexible fabric. Therefore, the multi-layer retention mechanism 102 can include the top layer 102a, control module 106, bottom layer 124, one or more boning mechanisms 163, one or more structural support pieces 161, one or more straps 126 and one or more locking mechanisms 168.

Referring still to FIG. 1E, in some embodiments, the bottom layer 124 can include and/or be coupled to a silicone overmold insert 121. In some embodiments, the silicone overmold insert 121 can be configured to receive one or more component mounting systems 120. In some embodiments, the silicone overmold insert 121 can be configured to be placed on a user's body part (e.g., a knee region, a lower back region, an elbow region, etc.). As shown, the component mounting system 120 can be coupled to a portion of the silicone overmold insert 121 and/or a portion of the top layer 102a. The component mounting system 120 is described in further detail below.

Referring again to FIG. 1E, in some embodiments, the component mounting system 120 can include a heat spreader 126 disposed between a plate 124 and a spacer 130. In some embodiments, the plate 124 can be configured to attach to the silicone overmold insert 121 on one side and to attach to the heat spreader 126 on another side. In an example, the plate 124 (e.g., a lower surface of the plate 124) can include (e.g., be coated with) an adhesive (e.g., a silicone adhesive) which can be configured to bond with a surface/layer of the silicone overmold insert 121. In some examples, the heat spreader 126 (e.g., an upper surface of the heat spreader) can include (e.g., be coated with) a primer layer that is configured to bond with an adhesive (e.g., another silicone adhesive) on another, opposite surface, of the plate 124 (e.g., the surface of the mounting plate facing the heat spreader 126). Additionally, the heat spreader 126 (e.g., a lower surface of the heat spreader) can include (e.g., be coated with) a primer layer configured to bond with an adhesive (e.g., a silicone adhesive) on a surface of the silicone overmold insert 121.

Referring again to FIG. 1E, in some embodiments, the spacer 130 can be positioned between the heat spreader 126 and heatsink 132. Additionally, a thermoelectric cooler (TEC) 128 can be located within a central opening of the spacer 130. The spacer 130 can also have at least one bottom opening and at least one on top opening located at a bottom portion and a top portion of the spacer 130, respectively. Each of the bottom and top openings can be configured to receive at least one screw 122/136 from the bottom and/or top of the spacer 130, respectively. In an example, at least one bottom screw 122 can be used to mount the plate 124 and the heat spreader 126 to the bottom portion of the spacer 130, where the plate 124 and heat spreader 126 can include corresponding mounting openings for the bottom screws 122. The openings through the heat spreader 126 can be aligned with the openings of the plate 124. The heatsink 132 can be placed above the spacer 130. In some embodiments, the heatsink 132 can be disposed flush against a top portion of the spacer 130. Furthermore a fan 134 can be disposed over the heatsink 132 and the spacer 130. In some embodiments, the heatsink 132 is secured between the spacer 130 and the fan 134, e.g., the heatsink 132 can be clamped down by the spacer 130 and the fan 134. In some embodiments, at least one top screw 136 can be used to mount the fan 134 to the spacer 130 through at least one opening of the fan 134 and a corresponding top opening of the spacer 130. In an example, the at least one opening of the fan 134 can be aligned with at least one top opening of the spacer 130. Thus, in some embodiments, the heatsink 132 can be held together between the fan 134 and spacer 130 by a force, e.g., a clamping pressure, between the fan 134 and the spacer 130 upon mounting the fan 134 to the spacer 130. The heatsink 132 can include an alignment feature that allows for an accurate placement of the heatsink 132 over the spacer 130. In an example, the alignment feature of the heatsink 132 can fit into a notch, e.g., corresponding alignment feature of the spacer 130, allowing for the heatsink 132 to lock in place along a horizontal direction.

Referring to FIG. 1E, in some embodiments, a cover 138 and cap 140 can be placed over the spacer 130, heatsink 132, fan 134 and a portion of the top layer 102a. In an example the cover 138 can secure the top layer 102a to the spacer 130. Furthermore, in some embodiments, the cover 138 can include one or more openings that can provide air circulation for the heatsink 132. In an example, the one or more openings may operate as vents (e.g., exhaust vents and/or intake vents). In some embodiments, the one or more vents in the cover 138 can be located along a wall portion of the cover 138. In some embodiments, the one or more vents of the cover 138 can be grouped into two groups of openings. In an example, one group of openings can be located at an opposite side from another group of openings along a wall portion of the cover 138. The component mounting system 120 can also include a cap 140. The cap 140 can be placed over the cover 138. The cap 140 can also include a locking mechanism that fits into a corresponding locking mechanism in the cover 138. In some embodiments, the cover 138 can extend down to and meet a bottom portion of the fan 134. The cap 140 can include one or more openings, which can also be referred to as a holes, slits or gap on a top portion of the cap 140. In an example, the one or more openings at the top portion of the cap 140 can be arranged in the shape of a hexagon and/or a honeycomb configuration. In some embodiments, the component mounting system 120 can be configured to draw air through the openings in the cap 140, by the fan 134, and air can be pushed to a central portion of the heatsink 132, where the air exits the component mounting system 120 out through one or more vents of the cover 138 (e.g., as described in FIG. 1D).

Components of the Temperature Modulation System

Each component from the temperature modulation system 104 of FIG. 1A is described below. For example, the TEC 128 of FIG. 1E is described in detail in FIG. 2. In another example, the heatsink 132 of FIG. 1E is described in detail in FIG. 3. Therefore, it can be understood that each component of the component mounting system above is described correspondingly in detail in below.

Figure 2:
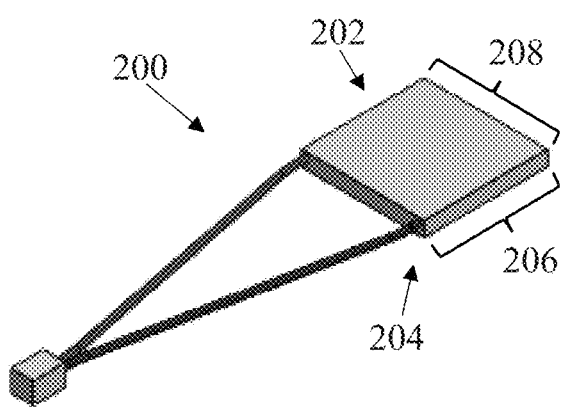
FIG. 2 illustrates a thermoelectric cooler (TEC), according to some embodiments.

FIG. 2 illustrates a thermoelectric cooler (TEC) 200, according to some embodiments. As used herein, the TEC 200 shown can be the same TEC used in FIG. 1E. In an embodiment, a TEC 200 can be selected based on its thermal conductivity rating. In an example, the inventors have found that a TEC 200 having a high thermal conductivity rating, e.g., approximately greater than or equal to the thermal conductivity of a ceramic material, can be used. The TEC 200 can have a top portion 202 and a bottom portion 204. In some embodiments, the length 206 of the TEC 200 can be approximately equal to its width 208. In an example, the TEC 200 can include 40 mm length 206 and 40 mm width 208. A thermal grease can be disposed between the heat spreader and the TEC 200, e.g., referring to the configuration shown in FIG. 1E. In an example, a thermal grease with a high thermal conductivity, e.g., in the range of approximately 1-15 w/mk (e.g., 1 w/mk), can be used. In an embodiment, a thermal grease from Halnzive company can be used.

Figure 3:
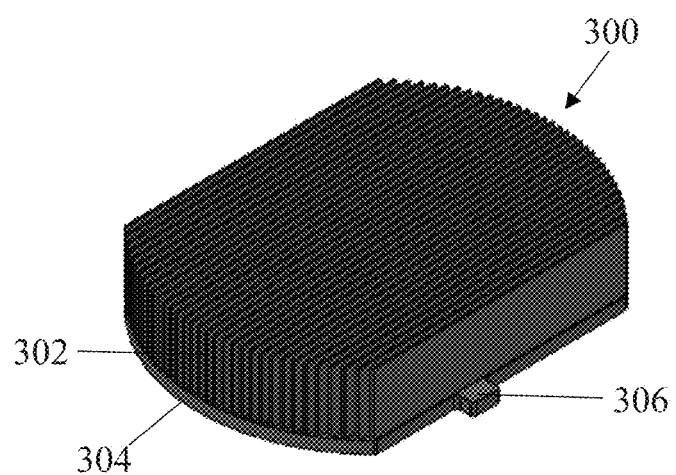
FIG. 3 illustrates a plan view of a heatsink, according to some embodiments.

FIG. 3 illustrates a plan view of the heatsink 300, according to some embodiments. As used herein, the heatsink 300 shown can be the same heatsink used in FIG. 1E. Referring to FIG. 3, the heatsink 300 can include a component and/or material configured to draw heat away the TEC and/or other components of the component mounting system. In some embodiments, the heatsink 300 includes a plurality of fins 302 extending from a base portion 304 of the heatsink 300. In some embodiments, the plurality of fins 302 can be formed through a skiving technique. In some embodiments, the plurality of fins 302 can be referred to as skived fins. In some embodiments, in contrast to using extrusion which is one way conventional heatsinks are formed, the entire heatsink 300 can be formed using a skiving technique. In some embodiments, the heatsink 300 can be referred to as a skived heatsink. In an example, a metal work skiving process can be used to form heatsink 300 and/or the plurality of fins 302. As referred to herein the plurality of fins 302 can also be referred to individually, e.g., each fin 302 or as one or more fins 302. In some embodiments, the heatsink 300 can include a first tab 306. In some embodiments, one or more tabs can be used. In some embodiments, the heatsink can include aluminum. In an example, the heatsink can include anodized aluminum. In some embodiments, the heatsink can include aluminum 6063.

Figure 4:
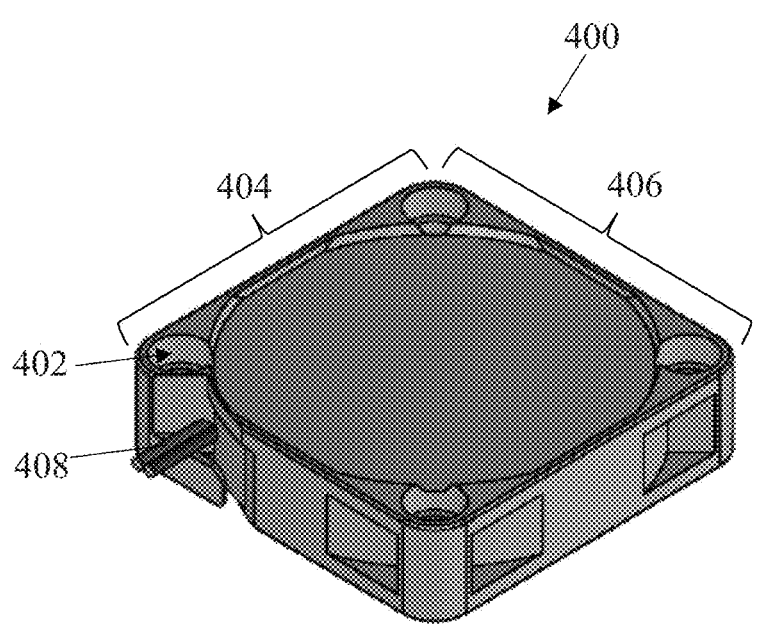
FIG. 4 illustrates a plan view of a fan, according to some embodiments.

FIG. 4 illustrates a plan view of a fan 400, according to some embodiments. As used herein, the fan 400 shown can be the same fan used in FIG. 1E. When active, the fan 400 can direct air away from the heatsink. In some embodiments, the fan 400 includes a plurality of openings 402. In some embodiments, the openings 402 can be configured to receive a screw for mounting the fan to the spacer described in FIGS. 1E and 5A-5D. In some embodiments, the width 404 of the fan 400 can be in a range of approximately 35-45 mm. In an example, the width 404 of the fan 400 can be approximately 40 mm. In some embodiments, the length 406 of the fan 400 can be in a range of approximately 35-45 mm. In an example, length 406 of the fan 400 can be approximately 40 mm. The fan 400 can include wires 408 for electrical power.

Figure 5A:
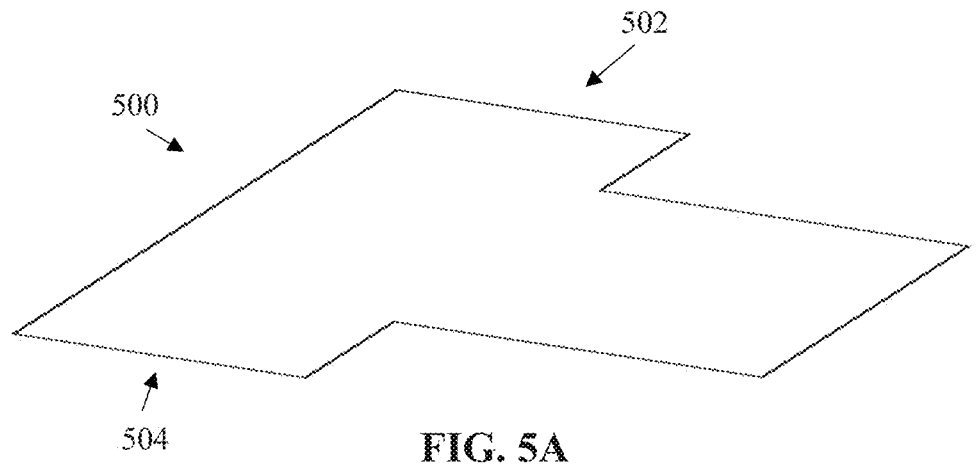
FIG. 5A illustrates a top view of a conductive flag, according to some embodiments.
Figure 5B:
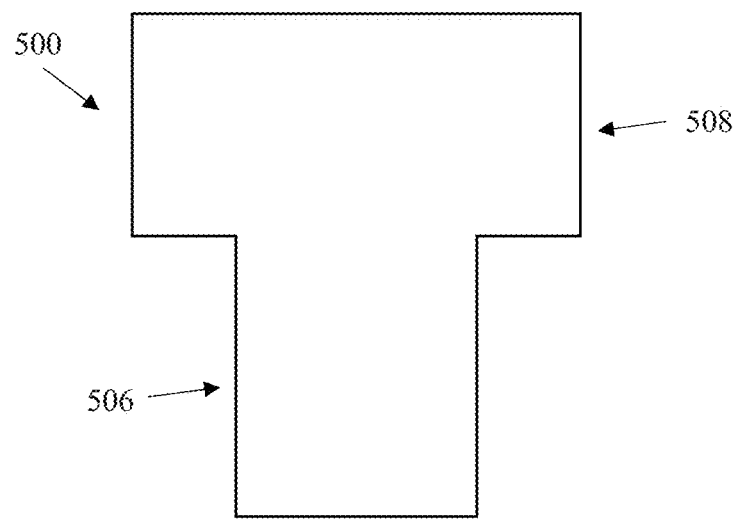
FIG. 5B illustrates a side view of the conductive flag from FIG. 5A, according to some embodiments.
Figure 5C:
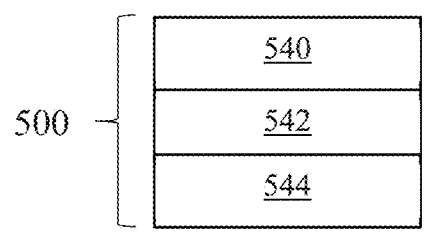
FIG. 5C illustrates a cross-sectional view of the conductive flag from FIG. 5A and FIG. 5B, according to some embodiments.

Referring to FIGS. 5A, 5B, and 5C various views of a conductive flag 500 are presented, according to some embodiments. In some embodiments, the flag 500 can have a top portion 502 and a bottom portion 504. In an example, the flag 500 may be "T" shaped. In an example, the flag may be 18 mm long by 16 mm wide.

Referring to FIG. 5A, a side view of the conductive flag 500 is presented, according to some embodiments. In some embodiments, a silicon-based adhesive can be disposed at the top portion 502 of the conductive flag 500. In some embodiments, the silicon-based adhesive can be configured to adhere the top portion 502 to the top portion 202 or the bottom portion 204 of the TEC 200. In some embodiments, the silicon-based adhesive can be configured to adhere the top portion 502 to a temperature sensor of the control module 106. For example, the silicon-based adhesive can adhere the top portion 502 to a temperature sensor of the control module 106 such that the flag 500 encloses (e.g., wraps around) the temperature sensor. In some embodiments, the flag 500 can be configured to spread temperature in a horizontal and vertical direction, e.g., along a x, y and z directions. In an embodiment, the flag 500 can be configured to provide an intermediate conductive medium for the temperature sensor to measure the temperature of the top portion 202 or the bottom portion 204 of the TEC 200. The flag 500 can conduct thermal energy from the TEC 200 to the temperature sensor such that the temperature offset between the TEC 200 and the temperature sensor is small or negligible. In an example, a small or negligible temperature offset may be 0.1-3.0° F. (e.g., 0.1-0.3° F.). In some embodiments, the heat spreader flag 500 can arrive as a roll at the beginning of a manufacturing process. In an embodiment, during manufacturing, the top portion 502 of the flag 500 can include a liner which can later be removed to expose the adhesive disposed at the top portion 502 of the flag 500.

Referring to FIG. 5B, a top view of the conductive flag 500 is presented, according to some embodiments. In some embodiments, the flag 500 can have a narrow end 506 and a wide end 508. The silicon-based adhesive can be configured to adhere the narrow end 506 of the top portion 502 to a temperature sensor. The silicon-based adhesive can be configured to adhere the wide end 508 of the top portion 502 to the top portion 202 or the bottom portion 204 of the TEC 200. In some embodiments, the wide end 508 of the top portion 502 can be adhered to the top portion 202 or the bottom portion 204 of the TEC 200 such that the flag 500 is located between the heat spreader 300 and the TEC 200.

Referring to FIG. 5C, a cross-sectional view of a diagram for the conductive flag 500 is presented, according to some embodiments. In some embodiments, the flag 500 can include 3 layers. In an example, the heat spreader can include a top layer 540, a middle layer 542 and a bottom layer 544. In some embodiments, the top layer 540 can include PET (polyethylene terephthalate) layer, the middle layer 542 can include a graphite/graphene layer and the bottom layer 546 can include another PET layer. In an example, the middle layer 542 can include a graphene layer which includes a synthetic graphite sheet. In some examples, the middle layer 542 can include of small particles (e.g., of graphene). In some embodiments, the graphene layer can include a metal based powder for thermal energy transfer. In an example, the flag 500 can include DSN5050-10DC10SB Synthetic Graphite Sheet from DASEN company.

Figure 6:
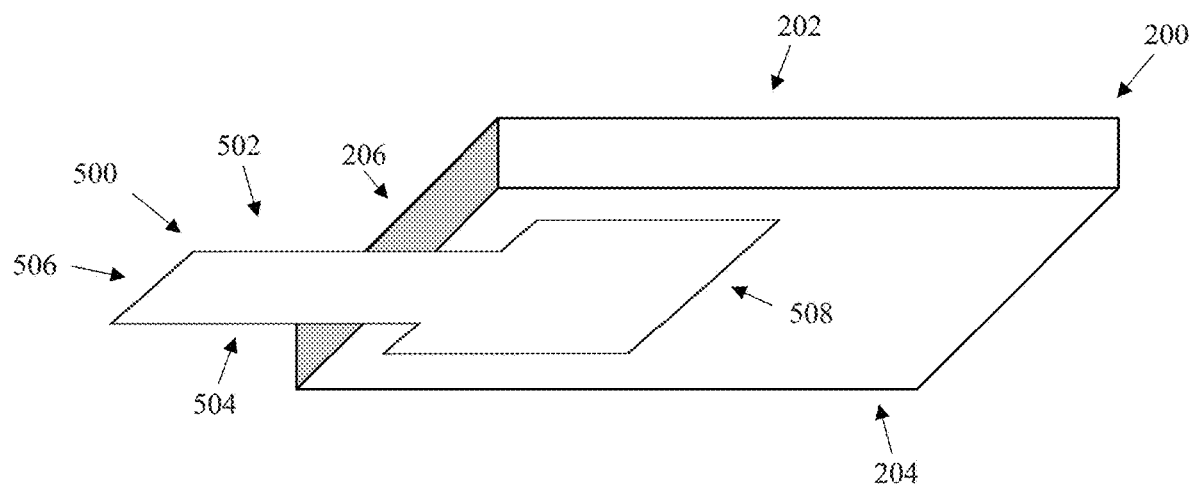
FIG. 6 illustrates a bottom view of a conductive flag adhered to a thermoelectric cooler (TEC), according to some embodiments.

Referring to FIG. 6, a bottom view of the conductive flag 500 adhered to the TEC 200 is presented, according to some embodiments. In some embodiments, the wide end 508 of the top portion 502 of the flag 500 can be coupled (e.g., adhered) to the bottom portion 204 of the TEC 200. In some embodiments, the narrow end 508 of the top portion 502 of the flag 500 can be coupled (e.g., adhered) to a temperature sensor, such that the top portion 502 encloses the temperature sensor in the conductive material comprising the flag 500. A temperature sensor may be adjacent or proximal to a side 206 of the TEC 200, such that the temperature sensor is located in a plane of the TEC 200 (e.g., between the top portion 202 and the bottom portion 204).

Temperature Control of a Temperature Therapy Device

Referring to FIG. 1A, the temperature modulation system 104 can function to provide an interfacial surface (e.g., between the temperature therapy device 100 and a body region of a user 112) having a controllable temperature. The temperature modulation system 104 can also function to provide a surface that can be placed against a body region (e.g., skin region) of a user 112 in an area where the user desires hot and/or cold therapy. The temperature modulation system 104 (e.g., in variations including a plurality of temperature modulation systems) can be connected to the power supply module 108 (e.g., by a direct electrical connection configured to supply electrical power), to the control module 106 (e.g., by a data connection configured to send and receive data, a wired connection, a wireless connection, etc.), and physically coupled to and/or retained by the multi-layer retention mechanism 102 (e.g., at the retention region of the multi-layer retention mechanism 102). In some embodiments, the power and/or data connections can be removable (e.g., via an electromechanical coupler). Connections can also be routed through the multi-layer retention mechanism 102 (e.g., between fabric layers of the retention mechanism, integrated into conductive thread of the retention mechanism, etc.). In some embodiments, connections can additionally or alternatively be sealed within the multi-layer retention mechanism 102 (e.g., between layers of the retention mechanism) using materials that provide a waterproof boundary that fully encloses the electrical connections (e.g., to avoid electrical shorting when the retention mechanism is in contact with water, sweat, and/or other liquids).

In some embodiments, the temperature therapy device 100 can include a plurality of temperature modulation systems 104. The plurality of temperature modulation systems 104 can be arranged in a predetermined pattern (e.g., defined by a pattern of retention regions at the retention mechanisms). As an example, the temperature therapy device 100 can include five temperature modulation systems 104 arranged in a substantially pentagonal array proximal the edges of an ovoid broad surface of the multi-layer retention mechanism 102. In some embodiments, the temperature therapy device 100 can include any suitable number of temperature modulation systems 104, arranged in any suitable manner (e.g., including modular, reconfigurable temperature modulation systems 104). As such, in some variations, multiple temperature modulation systems 104 can be repositioned relative to the multi-layer retention mechanism 102 by the user or another entity, in order to provide a customizable configuration of the temperature therapy device (e.g., for use on various body regions of the user in different customized configurations).

In some embodiments, the TEC 128 of the temperature modulation system 104 can provide a thermomechanical interface through which heat is exchanged with a body region of a user 112. The TEC 128 can optionally include an interface layer (e.g., a thermal pad, a gel layer, a thermal grease layer, etc.). The TEC 128 can include a contact surface (e.g., proximal surface to a body region of a user 112) that functions as the actively heated and/or cooled surface of the temperature modulation system 104. The contact surface can be driven to and/or maintained at a configured temperature (e.g., set by the control module 106, set by the user at a client application in communication with the control module 106, etc.). The contact surface of the TEC 128 can have any suitable shape including: triangular, circular, square, rectangular, etc. The TEC 128 can include a non-contact surface (e.g., distal surface from a body region of a user 112) that functions as the surface at which waste heat is rejected and/or from which heat is extracted (e.g., in cases wherein the contact surface is being heated and/or the temperature modulation system is operated in the heating mode). In some embodiments, the TEC 128 can be placed in direct or indirect contact with a temperature sensor 107. For example, the temperature sensor 107 may be coupled to the TEC 128 via an intermediate conductive flag as described herein. The temperature sensor 107 can enable automatic closed-loop control of the temperature at the contact surface of the TEC 128 via the control module 106 and/or another controller in communication with the control module 106 (e.g., a client application executing on a mobile device 110).

In some embodiments, the TEC 128 can be a thermoelectric cooling and/or heating device (e.g., a Peltier cooler and/or heater, any other suitable type of thermoelectric cooler/heater or panel, etc.), wherein an applied voltage generates a temperature differential between the contact surface and non-contact surface. The temperature differential between the contact surface and non-contact surface may be based on the applied voltage. As an example, the TEC 128 can include a Peltier thermoelectric module defining a rectilinear cross section (e.g., 40 mm×40 mm or any other suitable footprint) and having a defined thickness (e.g., 4.2 mm or any other suitable thickness), and adapted to receive a range of currents (e.g., between 0.5-2 A) at a specified voltage (e.g., approximately 15 V) that can be reversed in polarity in order to generate either a high temperature (e.g., 100-120° F.) or a low temperature (e.g., 40-60° F.) at the contact surface.

In some embodiments, the TEC 128 can include an internal void (e.g., a hollow interior of the layer, a set of tubes, etc.) through which a circulating fluid can be pumped by a pumping mechanism of the temperature modulation system 104. The circulating fluid can be heated and/or cooled to a controlled temperature (e.g., a high temperature, a low temperature, etc.).

Referring to FIG. 1A, the control module 106 can determine control instructions (e.g., received at an input device of the control module 106 or via a mobile device 110) and control the temperature modulation system(s) 104 according to the determined control instructions. In some embodiments, the control module 106 can receive control instructions and/or generate control instructions (e.g., at a mobile device platform or application, an integrated user interface, etc.). For example, the control module 106 may receive control instructions from a client application operating at a mobile device 110. The control module 106 can apply a control voltage to the temperature modulation system 104 such that a desired temperature (e.g., a high temperature, a low temperature, etc.) is generated at the contact surface of the TEC 128 and thereby at a body region of a user 112. In some embodiments, the control module 106 can include Proportional-Integral-Derivative control (PID) control methods. The control module 106 may duty-cycle the control voltage applied to the temperature modulation system 104 based on a difference between a temperature measured at the temperature modulation system 104 and a target temperature (e.g., temperature setpoint) of the temperature modulation system 104. The control module 106 can include a processor and/or a communications module. The control module 106 can be communicatively coupled to each temperature modulation system 104 (e.g., via physical data connection or a wireless data connection such as Bluetooth, etc.) of the temperature therapy device 100. In some embodiments, the control module 106 can be communicatively coupled to a mobile device 110 (e.g., via a Wi-Fi radio, Bluetooth, Bluetooth low-energy/BLE, or any other suitable wireless communication protocol, a wired connection, etc.). The mobile device 110 may be any one of a mobile computing device, a tablet computing device, a laptop computing device, or a desktop computing device. The mobile device 110 may be operated by a user of the temperature therapy device 100 or another individual (e.g., a therapy professional, doctor, etc.) As such, the control module 106 can be at least partially executable through a mobile application platform of a mobile device 110 of the user. In some embodiments, the temperature therapy device 100 can include a single control module 106 (or integrated control and power supply module 119) coupled to each temperature modulation system 104 of the temperature therapy device 100. For example, a single control module 106 can independently control five temperature modulation systems 104 of the temperature therapy device 100, such that the control module 106 can modulate each temperature modulation system 104 based on measured temperatures as described herein. In some embodiments, each temperature modulation system 104 can be coupled to a corresponding control module 106 (or integrated control and power supply module 119). In some embodiments, the temperature therapy device 100 can have any suitable correspondence between any number of control modules 106 and temperature modulation systems 104. The control module 106 is can be retained by the multi-layer retention mechanism 102 (e.g., sewn into the retention mechanism, coupled via a male/female interface, removably coupled and retained by a sleeve, etc.) and/or can be remote, removed, and/or separate from the multi-layer retention mechanism 102 (e.g., couplable via a removable connector, a wireless communication link, etc.).

Referring again to FIG. 1A, the control module 106 can include a temperature sensor 107 that that functions to monitor the temperature of the contact surface of the TEC 128. The output of the temperature sensor 107 (e.g., an analog or digital signal indicative of the temperature of the contact surface) can be provided to the control module 106 via a direct data connection (e.g., a serial bus, a double-ended signal transmission wire pair, etc.), but can be otherwise suitably coupled to the control module 106. The control module 106 can include a temperature sensor 107 corresponding to each temperature modulation system 104, but can additionally or alternatively include any suitable number of temperature sensors relative to the number of temperature modulation systems (e.g., multiple temperature sensors per temperature modulation system, a single temperature sensor arranged amid multiple temperature modulation systems, etc.). The temperature sensor 107 can include any suitable type of temperature sensor, such as contact sensors (e.g., thermocouples, thermistors, digital thermometers, analog thermometers, etc.) and non-contact sensors (e.g., infrared thermometers, radiative temperature sensors, scattered emission thermometers, etc.). The temperature sensor 107 can be arranged adjacent to (e.g., touching) the contact surface, proximal to the contact surface (e.g., retained by the retention mechanism within 1 mm, 2 mm, or any other suitable distance relative to the contact surface), adjacent to (e.g., touching) the non-contact surface, proximal the non-contact surface, and at any other suitable position relative to the surface(s) of the TEC 128. In some embodiments, the temperature sensor 107 can be adhered to the contact surface of the TEC 128 by a conductive flag as described herein.

In some embodiments, the temperature therapy device 100 can include a power supply module 108, which can provide electrical power to the temperature modulation system(s) 104 and the control module 106. The power supply module 108 can store energy to provide portable functionality (e.g., portability) to the system. The power supply module 108 can include a battery, power regulation circuitry, a charging interface, and/or any other suitable components for power supply and storage. The power supply module 108 can be coupled to the control module 106 (e.g., via direct electrical connection, an electrical cable, conductive stitching integrated into the retention mechanism, etc.) in a manner that promotes efficient routing relative to the multi-layer retention mechanism 102 and the temperature modulation system(s) 104 (e.g., to provide power via a direct electrical connection). In some embodiments, the power supply module 108 can be coupled (e.g., via the charging interface) to a source of grid power (e.g., alternating current, regulated direct-current, wall power, etc.). In an example, the power supply module 108 may supply a 7.4 V output. Any suitable voltage output may be supplied by the power supply module 108. The power supply module 108 can be otherwise suitably coupled to other system components in any suitable manner.

Referring to FIGS. 1A-1E, to effectively apply heating or cooling therapy, the temperature therapy device 100 requires a control method to map the temperature output by the TEC 128 of the temperature modulation system 104 to the temperature at a body region (e.g., skin) of a user 112. A temperature sensor 107 of the control module 106 can be configured to read the temperature at the area the temperature sensor 107 is located within the temperature therapy device 100. In some embodiments, as described herein, the temperature sensor 107 can be coupled adjacent to the contact surface of the TEC 128. In some embodiments, the temperature sensor 107 can be coupled proximal to the contact surface of the TEC 128, without direct contact to the contact surface of the TEC 128. In both embodiments, the temperature measured by the temperature sensor 107 may not be representative of the temperature at a body region of a user 112, as multiple components of the component mounting system 120 (e.g., a heat spreader, a plate, a silicone member, etc.) may insulate the contact surface of the TEC 128 from a body region of a user 112. Further, the body of the user (e.g., the circulatory system) can work to counter the thermal energy applied by the TEC 128, resulting in the measured temperature of the TEC 128 overstating the temperature of a body region during heating therapy and understating the temperature of a body region during cooling therapy. Accordingly, if control parameters of the temperature modulation system 104 and/or the control module 106 fail to account for this phenomenon, a body region of a user 112 may experience temperatures outside the desired therapeutic temperature ranges for heating and/or cooling. For example, while the temperature sensor 107 may read a temperature of 55° F. during cooling therapy applied by the temperature therapy device 100, the actual temperature at a body region of a user 112 may only be 64° F.

In some embodiments, the control module 106 can include instructions for one or more control methods to control and maintain the temperature(s) applied by the temperature therapy device 100. The control methods can be based on the temperature(s) measured by each temperature sensor 107 of the temperature therapy device 100. In some embodiments, the control module 106 (or a plurality of control modules 106) can control the temperature of each temperature modulation system 104 such that each TEC 128 can be driven to independently varying temperature setpoints based on the temperature reading(s) measured by the temperature sensor(s) 107. In some embodiments, the control module 106 (or a plurality of control modules 106) can control the temperature of each temperature modulation system 104 (e.g., by applying a control voltage) such that each TEC 128 can be driven to a common temperature setpoint based on temperature readings reported by the temperature sensor(s) 107.

In some embodiments, the control module 106 can process control instructions. The control instructions can be received at an input device of the control module 106 or received via a mobile device 110 communicatively coupled to the control module 106. The control instructions may include selection of a desired therapy (e.g., heating therapy or cooling therapy) a desired duration for the therapy, and/or an intensity level (e.g., a temperature setpoint) for the therapy. A range of intensity levels may be limited to configured therapeutic ranges for cooling therapy and/or heating therapy. In some embodiments, the therapeutic range for cooling therapy may be 50° F.-60° F. In some embodiments, the therapeutic range for heating therapy may be 104° F.-113° F. The intensity levels may be further limited within a therapeutic range. For example, the therapeutic range for heating therapy may be configured to be 104° F.-109° F., as users may indicate discomfort with the temperature therapy device 100 when the temperature at the body region of a user 112 exceeds 109° F. In some embodiments, the intensity level can be a discrete, preconfigured temperature level (e.g., temperature setpoint) selected from a plurality of discrete temperature levels. For cooling therapy, the intensity levels for selection by a user may include: 50° F., 53° F., 55° F., 57° F., and 60° F. For heating therapy, the intensity levels for selection by a user may include: 105° F., 106° F., 107° F., 108° F., and 109° F. Other intensity levels and/or other quantities of intensity levels may be configured. The control module 106 can receive control instructions indicating a selection from the plurality of intensity levels.

In some embodiments, the control instructions may include a manually configured temperature (e.g., temperature setpoint) for therapy. For example, the control module 106 may receive control instructions indicating a 54° F.

target temperature setpoint for cooling therapy. The manually configured temperature may be selected (e.g., by a user) from a range of temperatures, where the range of temperatures are segmented into discrete increments (e.g., 0.1° F., 0.5° F., 1° F., etc.). In some embodiments, where the control module 106 is configured to receive a manually configured temperature for therapy, the control module 106 can limit the range of temperature setpoints for the temperature modulation system(s) 104. The control module 106 may limit the range of temperature setpoints to the range of therapeutic temperatures. For example, the control module 106 may be configured to process received temperature inputs within the range of 50° F.-109° F. and discard received temperature inputs that are below 50° F. or above 109° F.

In some embodiments, based on receiving control instructions, the control module 106 can determine a control method. The control module 106 can include one or more distinct control methods for heating therapy and/or cooling therapy. For heating therapy and cooling therapy, the control methods can function to conserve power (e.g., battery life of the temperature therapy device 100) and maintain safe operating conditions for a user. A control method can be a heating control method or a cooling control method. For example, cooling therapy may include 3 distinct control methods during operation of the temperature therapy device. In some embodiments, a control method can define an offset between the temperature measured at the temperature sensor 107 and the resulting temperature at a body region of a user 112. A control method can include a time-varying model or a static model to map the temperature measured at the temperature sensor 107 to the resulting temperature at a body region of a user 112 during operation of temperature modulation system(s) 104.

In some embodiments, control methods can include a combination of cooling therapy and heating therapy. For example, a control method of the control module 106 may cause the temperature modulation system(s) 104 to heat a body region of a user 112 for a first duration time and cool the body region of the user 112 for a second duration of time. Alternately, the control module 106 may cool a body region of a user 112 for a first duration at a first temperature and cool the body region of the user for a second duration at a second temperature. Any suitable combination of heating therapy and cooling therapy at varying temperature setpoints for varying durations of time may be combined in a single therapy routine. A control method for a therapy routine may include control instructions defining cooling and/or heating therapy, including temperature setpoints for the TEC(s) 128 of the temperature therapy device 100 and durations of time associated with each temperature setpoint. The durations of time can include the time duration to achieve a temperature setpoint at a TEC 128 (e.g., measured by the temperature sensor 107) or include only the duration the TEC 128 is measured by the temperature sensor 107 to be at (or approximately equal to) the temperature setpoint. In an example, the duration can include the total time for therapy, including the time required for the temperature therapy device 100 to heat or cool to a temperature setpoint. A therapy routine can be associated with a recovery routine for a specific physical activity (e.g., tennis, baseball, basketball, mixed martial arts, etc.). In some embodiments, a temperature therapy device 100 can include a plurality of therapy routines stored in the control module 106, wherein at least a subset of the plurality of therapy routines are associated with a physical activity. For example, a control module 106 may include a therapy routine associated with a body region (e.g., an elbow) of a user that plays baseball. Additionally, a control module 106 may include a therapy routine associated with a body region (e.g., a knee) of a user that plays basketball).

Cooling Therapy Control of a Temperature Therapy Device

To provide cooling therapy, the control module 106 can include at least one cooling control method. A cooling control method of the control module 106 can enable the temperature therapy device 100 to apply cooling therapy to a body region of a user 112. Cooling therapy can include reaching therapeutic cooling temperatures at a body region of a user 112. The range of therapeutic cooling temperatures may include 50° F.-60° F. as described herein. In some embodiments, other temperature ranges for cooling therapy may be used.

In some embodiments, the cooling control method of the control module 106 can be based on a target temperature. The target temperature may be the desired temperature measured at the temperature sensor 107. The temperature measured at the temperature sensor 107 can be representative of the measured temperature at the contact surface (e.g., proximal to a body region of a user 112) of the TEC 128. According to the cooling control method, the control module 106 can function to drive the TEC 128 to the target temperature. The control module 106 may drive the TEC 128 to the target temperature (e.g., temperature setpoint) based on PID control methods. In some embodiments, constants for proportional gain, integral gain, and derivative gain of a PID algorithm can be selected based on combination of power conservation and time to cool a body region of a user. Based on the measured temperature of temperature sensor 107 and the target temperature for temperature sensor 107, the control module 106 can apply PID control methods to duty-cycle the control voltage (and corresponding power) applied to the TEC 128. The control module 106 may duty-cycle the control voltage applied to the TEC 128 to produce an average control voltage output in a range of 0%-100% of the maximum control voltage that can be output by the control module 106. For example, where the maximum control voltage output by the control module 106 is 7.4 V, duty-cycling the control voltage output to 60% would yield an average control voltage output of 4.4 V over a defined time period. In some embodiments, the target temperature can be a function of a selected temperature setpoint for a body region of a user 112, an offset (e.g., a time-varying offset), and a calibration value. The target temperature for cooling therapy by the temperature device 100 can be defined in Table 1 and Equation 1 as follows:

TABLE 1

Cooling Therapy Control Equation (Equation 1) Parameters

| | |
|---|---|
| Target Temperature | Target temperature measured by a temperature sensor |
| Body Temperature | Selected temperature setpoint for a body region |
| Offset(t) | Time-varying function of expected temperature difference between temperature measured by temperature sensor and temperature of a body region |
| Calibration | Calibration constant determined during manufacturing |

$$\text{Target Temperature} = \text{Body Temperature} - \text{Offset}(t) + \text{Calibration} \quad \text{Equation 1}$$

Equation 1 as described above may be defined in ° F. In some embodiments, alternate units of temperature (e.g., °

C.) can be used for Equation 1. As described herein, the "Target Temperature" described in Table 1 and Equation 1 can be the target temperature measured by temperature sensor 107. For example, according to Equation 1, the control module 106 can apply a control voltage to the TEC 128, cooling the contact surface of the TEC 128 such that the measured temperature at temperature sensor 107 is the "Target Temperature".

In some embodiments, the "Body Temperature" constant described in Table 1 and Equation 1 can be a temperature setpoint for the temperature therapy device 100 included in received control instructions. For example, based on receiving control instructions at the control module 106 (e.g., from a user) indicating a temperature setpoint of 55° F., the "Body Temperature" constant can be configured to 55 in Equation 1.

In some embodiments, the "Offset(t)" function described in Table 1 and Equation 1 can be a time-varying function. The time-varying function may be a piecewise linear function of time. The time-varying function can represent the expected temperature difference between the measured temperature of temperature sensor 107 (e.g., the temperature of the TEC 128) and the expected temperature at a body region of a user 112 during operation of the temperature therapy device. The "Offset(t)" function can account for a body region's resistance (e.g., through blood circulation) to temperature change over time, as well as the difference in temperature at a body region and at the TEC 128 due to thermal buffering effects from components of the component mounting system 120 (e.g., a heat spreader, a plate, a silicone member, etc.). In some embodiments, the "Offset(t)" function may be defined by Equation 2 as follows:

$$\text{Offset}(t) = \begin{cases} 21 - \dfrac{t}{60}; t \leq 300 \\ 19.2 - \dfrac{t}{90}; 300 < t \leq 600 \\ 16.5 - \dfrac{t}{150}; 600 < t \end{cases} \quad \text{Equation 2}$$

For Equation 2 as described above, t can be defined in seconds and Offset(t) can be defined in ° F. For the Offset(t) function, t=0 can be the time at which a user activates the temperature therapy device 100 for cooling therapy. In some embodiments, t=0 can be the time at which the control module 106 begins to apply a control voltage to the TEC 128 to initiate cooling therapy. In some embodiments, t may reset to t=0 when the temperature therapy device 100 is deactivated, powered off, and/or otherwise removed from a body region of a user 112. In some embodiments, alternate units of time (e.g., minutes) can be used for t and/or alternate units of temperature (e.g., ° C.) can be used for Equation 2. In some embodiments, alternate functions (e.g., a non-linear function, non-piecewise function, constant function, etc.) can be used for Offset(t). As an example, for t=120, Offset(t) can equal 19° F. As another example, for t=360, Offset(t) can equal 15.2° F. As another example, for t=750, Offset(t) can equal 11.5° F. The Offset(t) function can function to prevent temperature drift between the measured temperature at the temperature sensor 107 and the actual temperature at a body region of a user 112, as the relationship between the measured temperature and the actual temperature at a body region may not be static over a duration of cooling therapy. As an example, the difference between measured temperature at the temperature sensor 107 and the actual temperature at a body region may be 20° F. at t=150, whereas the difference may be 10° F. t=800.

In some embodiments, the "Calibration" constant described in Table 1 and Equation 1 can be a temperature measurement constant defined for the temperature therapy device 100 and control module 106. The "Calibration" constant may be configured individually for each temperature sensor 107, each temperature modulation system 104 (and TEC 128), or each control module 106 of the temperature therapy device 100. In some embodiments, the "Calibration" constant may be configured based on quality control method during manufacturing of the temperature therapy device 100. The quality control method for determining the "Calibration" constant for each temperature modulation system 104 and control module 106 is described herein in the sub-section title "Determining a Calibration Factor for a Temperature Therapy Device". The "Calibration" constant may function to account for manufacturing defects in the component mounting system 120 (e.g., thermal grease application variation, plate thickness variation, etc.) such that difference between the temperature measured at the temperature sensor 107 and the temperature of a body region of a user 112 vary beyond an expected temperature range (e.g., 5° F., 7° F., 10° F., etc.). As an example, if the expected temperature difference between the temperature measured at the temperature sensor 107 and the temperature of a body region of a user 112 during cooling is 8° F. and the measured temperature difference is 6° F., the "Calibration" constant may be configured to 2° F. As another example, if the expected temperature difference is 8° F. and the measured temperature difference is 11° F., the "Calibration" constant may be configured to −3° F. By including the "Calibration" constant, the control module 106 can cool the TEC 128 to the (approximate) temperature setpoint included in the received control instructions based on measurements of the temperature sensor 107.

In some embodiments, the control module 106 can initiate cooling therapy based on receiving control instructions. The control instructions can include a temperature setpoint for the temperature therapy device 100, where the temperature setpoint can be selected from one or more discrete, preconfigured temperature levels or manually configured as described herein. Based on receiving control instructions including a temperature setpoint, the control module 106 can apply a control voltage to the TEC 128 according to the "Target Temperature" of Equation 1. As an example, for a "Body Temperature" of 52° F., t=360, and "Calibration" constant of 2° F., the control module 106 can target a measured temperature of 38.8° F. at the temperature sensor 107. The control module 106 can duty-cycle the control voltage applied to the TEC 128 based on difference between the measured temperature at the temperature sensor 107 and the "Target Temperature" for the temperature sensor 107. The control module 106 can duty-cycle the control voltage based on PID control techniques to minimize the difference between the measured temperature at the temperature sensor 107 and the "Target Temperature" for the temperature sensor 107 as described herein. For example, as the measured temperature approaches the "Target Temperature", the control module 106 can duty-cycle the control voltage to 70% of the maximum control voltage, enabling the temperature therapy device 100 to conserve power (e.g., battery life for the power supply module 108) and approach the "Target Temperature" without significantly surpassing the "Target Temperature". As the measured temperature of the temperature sensor 107 approaches and/or reaches the "Target Temperature", the control module 106 can duty-cycle the control voltage such that the measured temperature at the temperature sensor 107 stabilizes about the "Target Temperature". Based on stabilizing the measured temperature, the control module 106 can enable cooling therapy at approximately the selected temperature setpoint.

Heating Therapy Control of a Temperature Therapy Device

To provide heating therapy, the control module 106 can include at least one heating control method. A heating control method of the control module 106 can enable the temperature therapy device 100 to apply heating therapy to a body region of a user 112. Heating therapy can include reaching therapeutic heating temperatures at a body region of a user 112. The range of therapeutic cooling temperatures may include 104° F.-113° F. as described herein. In some embodiments, other temperature ranges for heating therapy may be used (e.g., 104° F.-109° F.).

In some embodiments, the heating control method of the control module 106 can be based on a target temperature. The target temperature may be the desired temperature measured at the temperature sensor 107. The temperature measured at the temperature sensor 107 can be representative of the measured temperature at the contact surface (e.g., proximal to a body region of a user 112) of the TEC 128. According to the heating control method, the control module 106 can function to drive the TEC 128 to the target temperature. The control module 106 may drive the TEC 128 to the target temperature (e.g., temperature setpoint) based on PID control methods. In some embodiments, constants for proportional gain, integral gain, and derivative gain of a PID algorithm can be selected based on combination of power conservation and time to heat a body region of a user 112. Based on the measured temperature of temperature sensor 107 and the target temperature for temperature sensor 107, the control module 106 can apply PID control methods to duty-cycle the control voltage (and corresponding power) applied to the TEC 128. The control module 106 may duty-cycle the control voltage applied to the TEC 128 on a range of 0%-100% of the maximum control voltage that can be output by the control module 106. For example, where the maximum control voltage output by the control module 106 is 5 V, duty-cycling the control voltage output to 80% would yield an average control voltage output of 4 V over a defined time period. In some embodiments, the target temperature can be a function of a selected temperature setpoint for a body region of a user 112, an offset (e.g., a constant offset), and a calibration value. The target temperature for heating therapy by the temperature device 100 can be defined in Table 2 and Equation 3 as follows:

TABLE 2

Heating Therapy Control Equation (Equation 3) Parameters

| | |
|---|---|
| Target Temperature | Target temperature measured by a temperature sensor |
| Body Temperature | Selected temperature setpoint for a body region |
| Offset | Constant function of expected temperature difference between temperature measured by temperature sensor and temperature of a body region |
| Calibration | Calibration constant determined during manufacturing |

Target Temperature=Body Temperature+Offset+Calibration   Equation 3

Equation 3 as described above may be defined in ° F. In some embodiments, alternate units of temperature (e.g., ° C.) can be used for Equation 3. As described herein, the "Target Temperature" described in Table 2 and Equation 3 can be the target temperature measured by temperature sensor 107. For example, according to Equation 3, the control module 106 can apply a control voltage to the TEC 128, heating the contact surface of the TEC 128 such that the measured temperature at temperature sensor 107 is the "Target Temperature".

In some embodiments, the "Body Temperature" constant described in Table 2 and Equation 3 can be a temperature setpoint for the temperature therapy device 100 included in received control instructions. For example, based on receiving control instructions at the control module 106 (e.g., from a user) indicating a temperature setpoint of 105° F., the "Body Temperature" constant can be configured to 105 in Equation 1.

In some embodiments, the "Offset" constant described in Table 1 and Equation 1 can be a constant function that represents the expected temperature difference between the measured temperature of temperature sensor 107 (e.g., the temperature of the TEC 128) and the expected temperature at a body region of a user 112 during operation of the temperature therapy device. In some embodiments, the "Offset" constant may be the measured temperature of temperature sensor 107 (e.g., the temperature of the TEC 128) minus the expected temperature at a body region of a user 112. In other embodiments, the "Offset" constant may be the expected temperature at a body region of a user 112 minus the measured temperature of temperature sensor 107 (e.g., the temperature of the TEC 128). Accordingly, the sign (+/−) of the "Offset" constant may be selected as described herein. The "Offset" constant can account for a body region's resistance (e.g., through blood circulation) to temperature change over time, as well as the difference in temperature at a body region and at the TEC 128 due to thermal buffering effects from components of the component mounting system 120 (e.g., a heat spreader, a plate, a silicone member, etc.). In some embodiments, the "Offset" constant may be equal to 8° F. Alternate "Offset" constant values (e.g., 5° F., 10° F., etc.) may be defined to represent the relationship between the measured temperature at the temperature sensor 107 and the actual temperature of a body region of a user 112.

In some embodiments, the "Calibration" constant described in Table 2 and Equation 3 can be a temperature measurement constant defined for the temperature therapy device 100 and control module 106, as described above. For example, the "Calibration" constant may be configured individually for each temperature sensor 107, each temperature modulation system 104 (and TEC 128), or each control module 106 of the temperature therapy device 100. In some embodiments, the "Calibration" constant may be configured based on quality control test during manufacturing of the temperature therapy device 100. The "Calibration" constant may function to account for manufacturing defects in the component mounting system 120 (e.g., thermal grease application variation, plate thickness variation, etc.) such that difference between the temperature measured at the temperature sensor 107 and the temperature of a body region of a user 112 vary beyond an expected temperature range (e.g., 5° F., 7° F., 10° F., etc.). As an example, if the expected temperature difference between the temperature measured at the temperature sensor 107 and the temperature of a body region of a user 112 during cooling is 8° F. and the measured temperature difference is 6° F., the "Calibration" constant may be configured to 2° F. As another example, if the expected temperature difference is 8° F. and the measured temperature difference is 11° F., the "Calibration" constant may be configured to −3° F. By including the "Calibration" constant, the control module 106 can cool the TEC 128 to the (approximate) temperature setpoint included in the received control instructions based on measurements of the temperature sensor 107.

In some embodiments, the control module 106 can initiate heating therapy based on receiving control instructions. The control instructions can include a temperature setpoint for the temperature therapy device 100, where the temperature setpoint can be selected from one or more discrete, preconfigured temperature levels or manually configured as described herein. Based on receiving control instructions including a temperature setpoint, the control module 106 can apply a control voltage to the TEC 128 according to the "Target Temperature" of Equation 1. As an example, for a "Body Temperature" of 105° F., an "Offset" of 8° F., and "Calibration" constant of −3° F., the control module 106 would target a measured temperature of 110° F. at the temperature sensor 107. The control module 106 can duty-cycle the control voltage applied to the TEC 128 based on difference between the measured temperature at the temperature sensor 107 and the "Target Temperature" for the temperature sensor 107. The control module 106 can duty-cycle the control voltage based on PID control techniques to minimize the difference between the measured temperature at the temperature sensor 107 and the "Target Temperature" for the temperature sensor 107 as described herein. For example, as the measured temperature approaches the "Target Temperature", the control module 106 can duty-cycle the control voltage such that the average control voltage is 70% of the maximum control voltage, enabling the temperature therapy device 100 to conserve power (e.g., battery life for the power supply module 108) and approach the "Target Temperature" without significantly surpassing the "Target Temperature". Example PID control techniques may include those described by Borase, R. P., et al. A review of PID control, tuning methods and applications. *Int. J. Dynam. Control* 9, 818-827 (2021). As the measured temperature of the temperature sensor 107 approaches and/or reaches the "Target Temperature", the control module 106 can duty-cycle the control voltage such that the measured temperature at the temperature sensor 107 stabilizes about the "Target Temperature". Based on stabilizing the measured temperature, the control module 106 can enable heating therapy at approximately the selected temperature setpoint.

Temperature Control Method for a Temperature Therapy Device

Figure 7:
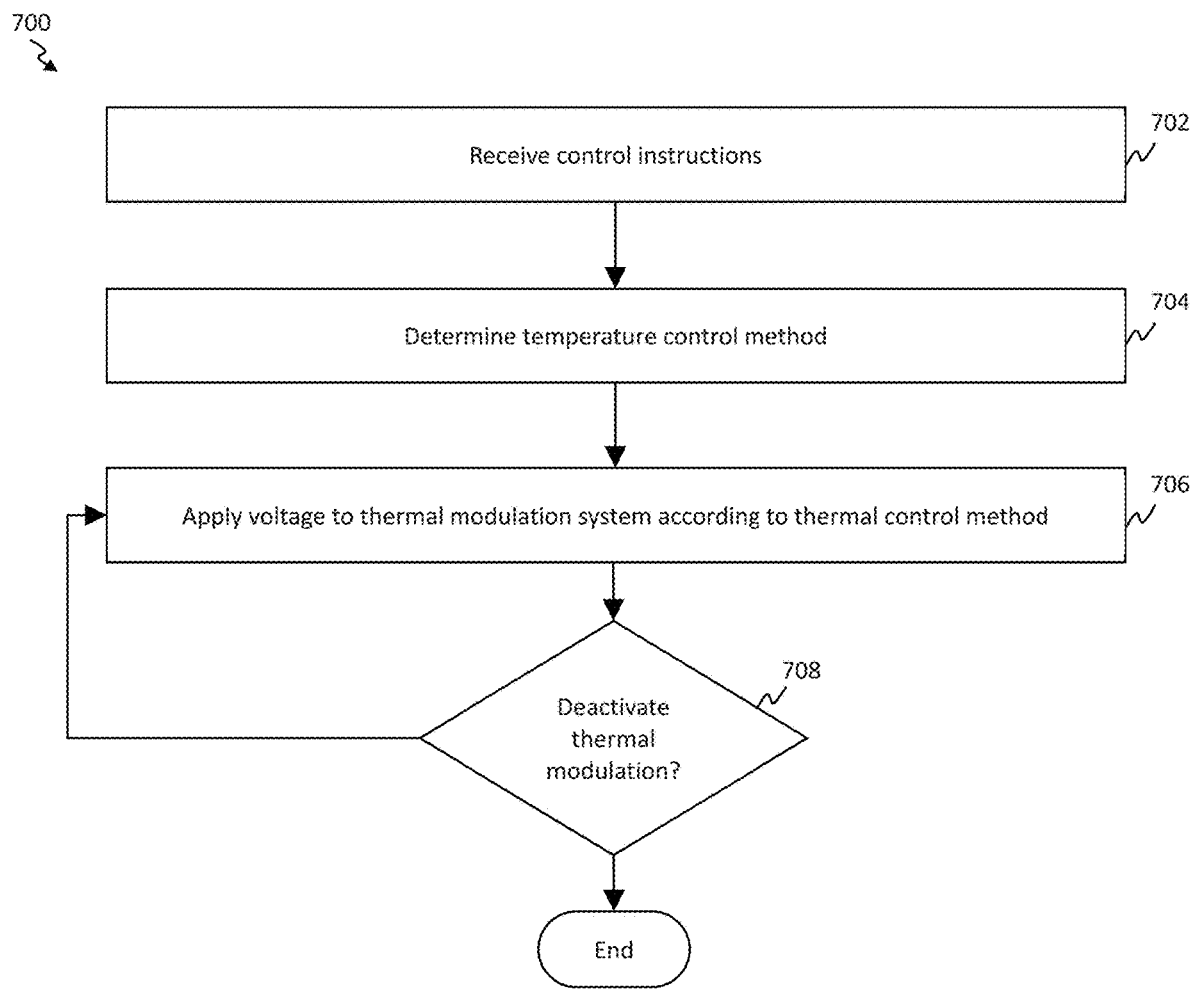
FIG. 7 illustrates a flowchart for a temperature control method of an exemplary temperature therapy device, according to some embodiments.

To apply the cooling control methods or heating control methods as described herein, the temperature therapy device 100 can apply a temperature control method. FIG. 7 illustrates a flowchart for a temperature control method 700 of an exemplary temperature therapy device 100, according to some embodiments. A control module 106 (or a plurality of control modules 106) can apply the temperature control method 700 as described herein to one or more temperature modulation systems 104 to enable cooling or heating therapy.

At step 702, the control module 106 can receive control instructions. The control instructions can include a temperature setpoint for therapy at a body region of the user 112. In some embodiments, the control instructions can include a duration for therapy at the body region of the user 112. The control instructions can be received at an input device of the control module 106 or received via a mobile device 110 communicatively coupled to the control module 106 as described here. The control module 106 can receive control instructions (or other signals) indicating selection of a preconfigured temperature setpoint using any suitable input interface or device (e.g., discrete button inputs, switches, touch screen, etc.).

At step 704, the control module 106 can determine the temperature control method for the temperature therapy device 100. The control module 106 can determine a cooling control method or a heating control method based on the temperature setpoint included in the received control instructions. In some embodiments, the control module 106 may determine a cooling control method or a heating control method based on comparing the temperature setpoint to one or more temperature thresholds or ranges. For example, if the temperature setpoint is equal to or below 60° F., the control module 106 can configure the cooling control method as described herein as the temperature control method for the temperature therapy device. Additionally, for example, if the temperature setpoint is within (or equal to) the temperature range of 104° F.-109° F., the control module 106 can configure the heating control method as described herein as the temperature control method for the temperature therapy device 100. In some embodiments, the received control instructions can indicate a cooling control method or a heating control method. For example, if the temperature setpoint is selected from one or more preconfigured temperature setpoint, the selection of a preconfigured temperature setpoint of 50° F. can indicate a cooling control method for cooling therapy.

At step 706, the control module 106 can apply a control voltage to a temperature modulation system 104 according to the determined temperature control method (e.g., the cooling control method or the heating control method). The control module 106 can apply a control voltage to the TEC 128 of the temperature modulation system 104 based on the "Target Temperature" determined as a function of described in Equation 1 and Equation 3 for the determined temperature control method. In some embodiments, the control module 106 can duty-cycle the control voltage applied to the TEC 128 based on PID control techniques to minimize the difference between the temperature measured at the temperature sensor 107 and the target temperature for the temperature sensor 107.

At step 708, the control module 106 can determine whether to deactivate thermal modulation for a temperature modulation system 104. The control module 106 can determine to deactivate thermal modulation (e.g., cooling or heating of the TEC 128) based on an expiry of a duration for therapy (e.g., as received in step 702). For example, if a user configures a duration of 20 minutes for therapy, the control module 106 can deactivate thermal modulation of the temperature modulation system 104 based on an expiry of the 20 minute duration. In some embodiments, the duration for therapy configured by a user can correspond to a duration the temperature modulation system is active (e.g., caused to heat or cool by the control module 106) or a duration the temperature measured at the temperature sensor 107 is approximately the "Target Temperature". In some embodiments, the control module 106 can determine to deactivate thermal modulation based on one or more received inputs. Inputs may be received at the temperature therapy device 100 (e.g., via an input device coupled to the control module 106) or via a computing device (e.g., the mobile computing device 110) communicatively coupled to the temperature therapy device 100.

Determining a Calibration Factor for a Temperature Therapy Device

A temperature therapy device 100 (and the included control module 106) can require calibration during a manufacturing process to validate temperature measurement capabilities. Such calibration can be necessary to ensure proper operation of the temperature therapy device 100, including accurate temperature measurement and controlled temperature modulation to provide cooling or heating therapy. Manufacturing defects (e.g., thermal grease application variation, plate thickness variation, temperature sensor sensitivity variation, etc.) can lead to variation in the expected temperature difference between temperature(s) measured by the temperature sensor(s) 107 and the temperature at a body region of a user 112. As such, the control module 106 can be configured with calibration factors (e.g., the "Calibration" constants as described herein for Equation 1 and Equation 3) for each temperature sensor 107 to account for potential manufacturing defects in the temperature therapy device 100. To calibrate a temperature therapy device 100, the temperature therapy device 100 may be placed on a calibration fixture. The calibration fixture may include one or more temperature sensors (e.g., infrared temperature sensors), wherein each temperature sensor can measure the temperature at a silicone overmold insert 121 of each component mounting system 120 of the temperature therapy device 100. For example, for a temperature therapy device 100 including five component mounting systems 120 (and five corresponding temperature modulation systems 104), the calibration fixture can include five infrared temperature sensors to measure the temperature at each of the silicone overmold inserts 121. In some embodiments, the calibration fixture may couple to each temperature sensor 107 of the temperature therapy device to monitor the temperature measured by each temperature sensor 107.

In some embodiments, based on being coupled to the calibration fixture, the temperature therapy device 100 can be activated for a heating therapy cycle and a cooling therapy cycle. For a heating therapy cycle, the control module 106 of the temperature therapy device 100 can be configured to a temperature (e.g., 105° F.) within the therapeutic heating range (e.g., 104° F.-109° F.). For a cooling therapy cycle, the control module 106 of the temperature therapy device 100 can be configured to a temperature (e.g., 105° F.) within the therapeutic heating range (e.g., 104° F.-109° F.). Based on activating the therapy device for a heating therapy cycle or a cooling therapy cycle, the calibration fixture can monitor the temperatures measured at each temperature sensor 107 and each temperature sensor of the calibration fixture. The calibration fixture can compare the measured temperatures during heating and cooling of the temperature therapy device. The calibration fixture may be configured with an expected temperature difference between the temperature(s) measured at each temperature sensor 107 (e.g., the TEC temperature) and each temperature sensor of the calibration fixture (e.g., silicone member temperature). For example, the calibration fixture can be configured to expect a 2° F. temperature difference (e.g., the difference of TEC temperature and silicone member temperature) for the heating therapy cycle and a 6° F. temperature difference (e.g., the difference silicone member temperature and TEC temperature) for the cooling therapy cycle. Based on measured variation from the expected temperature difference for the heating therapy cycle and the cooling therapy cycle, the control module 106 may be configured with a calibration factor (e.g., "Calibration" constant as described herein) for the heating control method and the cooling control method as described herein. The control module may be configured with a calibration factor for the heating control method and the cooling control method such that the expected temperature difference is satisfied. For example, for a heating therapy cycle with an expected temperature difference of 2° F. and a measured temperature difference of 7° F., the calibration factor can be configured as −5° F. In some embodiments, a calibration factor can be configured independently for each component mounting system 120 (and corresponding temperature modulation system 104). In some embodiments, a calibration factor can be configured independently for each temperature sensor 107 of the temperature therapy device 100.

Some embodiments of a temperature therapy device including a TEC have been described. A TEC is one example of a temperature control (e.g., heating and/or cooling) component that may be used in the temperature therapy device (e.g., temperature therapy device 100). In some embodiments, one or more heating and/or cooling components other than a TEC may be used. For example, a Peltier device, a Peltier heater, a Peltier heat pump, and/or any other suitable heating and/or cooling component may be used.

Some non-limiting examples of a temperature therapy device 100 have been described. Additional embodiments of temperature therapy devices are described in U.S. Provisional Patent Application No. 63/090,987 which is incorporated by reference herein. Furthermore, some non-limiting examples of components of a temperature therapy device have been described. Additional embodiments of such components, including flexible thermal spreaders (e.g., heat spreader 126), heating and/or cooling elements (e.g., TEC 128), flexible substrates (e.g., flexible layers of a multi-layer retention mechanism 102), and coupling materials (e.g., adhesives, tapes, etc.) are also described in U.S. Provisional Patent Application No. 63/090,987.

Computer Systems

Figure 8:
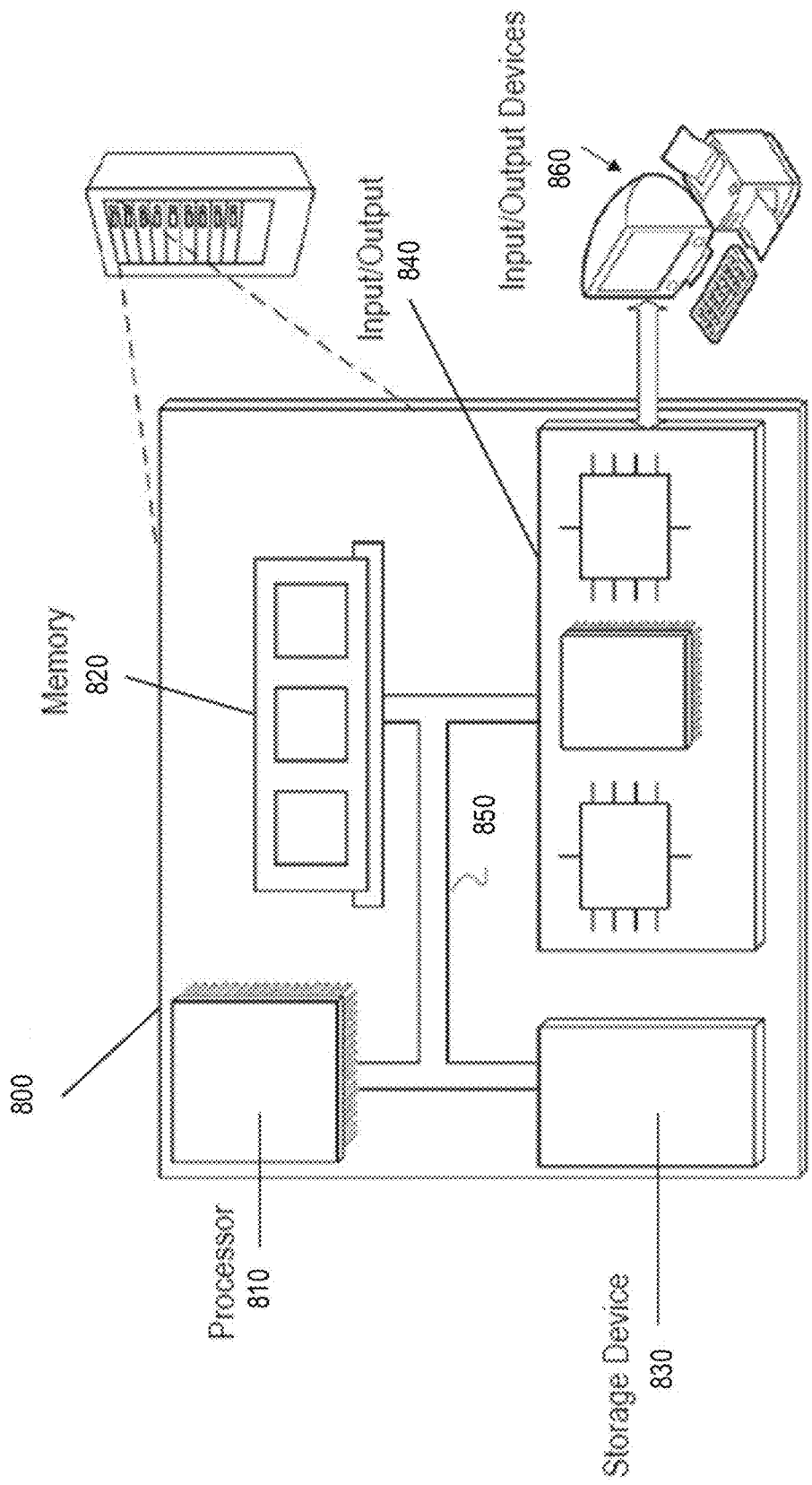
FIG. 8 is a block diagram of an example computer system, according to some embodiments.

FIG. 8 is a block diagram of an example computer system 800 that may be used in implementing the technology described in this document. General-purpose computers, network appliances, mobile devices, or other electronic systems may also include at least portions of the system 800. The system 800 includes a processor 810, a memory 820, a storage device 830, and an input/output device 840. Each of the components 810, 820, 830, and 840 may be interconnected, for example, using a system bus 850. The processor 810 is capable of processing instructions for execution within the system 800. In some implementations, the processor 810 is a single-threaded processor. In some implementations, the processor 810 is a multi-threaded processor. The processor 810 is capable of processing instructions stored in the memory 820 or on the storage device 830.

The memory 820 stores information within the system 800. In some implementations, the memory 820 is a non-transitory computer-readable medium. In some implementations, the memory 820 is a volatile memory unit. In some implementations, the memory 820 is a non-volatile memory unit.

The storage device 830 is capable of providing mass storage for the system 800. In some implementations, the storage device 830 is a non-transitory computer-readable medium. In various different implementations, the storage device 830 may include, for example, a hard disk device, an optical disk device, a solid-date drive, a flash drive, or some other large capacity storage device. For example, the storage device may store long-term data (e.g., database data, file system data, etc.). The input/output device 840 provides input/output operations for the system 800. In some implementations, the input/output device 840 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 860. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 830 may be implemented in a distributed way over a network, for example as a server farm or a set of widely distributed servers, or may be implemented in a single computing device.

Although an example processing system has been described in FIG. 8, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

Measurements, sizes, amounts, and the like may be presented herein in a range format. The description in range format is provided merely for convenience and brevity and should not be construed as an inflexible limitation on the scope of the invention. Accordingly, the description of a range should be considered to have specifically disclosed all the possible subranges as well as individual numerical values within that range. For example, description of a range such as 1-20 meters should be considered to have specifically disclosed subranges such as 1 meter, 2 meters, 1-2 meters, less than 2 meters, 10-11 meters, 10-12 meters, 10-13 meters, 10-14 meters, 11-12 meters, 11-13 meters, etc.

Furthermore, connections between components or systems within the figures are not intended to be limited to direct connections. Rather, data or signals between these components may be modified, re-formatted, or otherwise changed by intermediary components. Also, additional or fewer connections may be used. The terms "coupled," "connected," or "communicatively coupled" shall be understood to include direct connections, indirect connections through one or more intermediary devices, wireless connections, and so forth.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A wearable personal temperature therapy system for placement at a body region of a user, comprising:
   a retention mechanism;
   a plurality of temperature modulation systems attached to the retention mechanism, wherein each of the plurality of temperature modulation systems comprises a thermoelectric cooler having a first side and a second side opposing the first side;
   a plurality of temperature sensors;
   a plurality of conductive flags,
      wherein each of the plurality of conductive flags comprises a thermally conductive material, has a first side and a second side opposing the first side, and has a first end and a second end, wherein the first side comprises an adhesive material, and
   wherein for each of the plurality of conductive flags, the first side of the first end is adhered to the first side of a respective thermoelectric cooler of the plurality of thermoelectric coolers, wherein the first side of the second end is adhered to a respective temperature sensor of the plurality of temperature sensors, wherein a temperature differential between the first side of the respective thermoelectric cooler and the first side of the second end is configured to be less than 3.0 degrees Fahrenheit, wherein a surface area of the first side of the respective conductive flag is less than a surface area of the first side of the respective thermoelectric cooler; and
   a control module electrically coupled to each of the plurality of temperature modulation systems and each of the plurality of temperature sensors, wherein each of the plurality of temperature modulation systems is operable between a cooling mode and a heating mode based on a control voltage applied to the thermoelectric cooler of the respective temperature modulation system.

2. The system of claim 1, wherein the thermoelectric coolers of the plurality of temperature modulation systems are in thermal contact with the retention mechanism at the first sides of the thermoelectric coolers.

3. The system of claim 1, wherein for each of the plurality of conductive flags, the temperature sensor coupled to the respective conductive flag is positioned in a plane with the thermoelectric cooler coupled to the respective conductive flag.

4. The system of claim 1, wherein the control module is configured to control the plurality of temperature modulation systems based on outputs of the plurality of temperature sensors.

5. The system of claim 4, wherein in the heating mode, the control module is configured to duty cycle the control voltage based on a target temperature, wherein the target temperature is determined based on one or more of: a temperature setpoint, a constant offset, and a calibration constant.

6. The system of claim 4, wherein in the cooling mode, the control module is configured to duty cycle the control voltage based on a target temperature, wherein the target temperature is determined based on one or more of: a temperature setpoint, a time-based offset, and a calibration constant.

7. The system of claim 1, wherein in the heating mode, the control module is configured to maintain a temperature within a range of 104-109° F. at the retention mechanism.

8. The system of claim 1, wherein in the cooling mode, the control module is configured to maintain a temperature within a range of 50-60° F. at the retention mechanism.

9. The system of claim 1, wherein each of the conductive flags is configured to conduct thermal energy between the respective thermoelectric cooler and the respective temperature sensor.

* * * * *